United States Patent
Andersen et al.

(10) Patent No.: US 11,534,554 B2
(45) Date of Patent: Dec. 27, 2022

(54) ROTARY DOSAGE SENSING MODULE FOR AND IN A DISPOSABLE PEN DRUG DELIVERY DEVICE

(71) Applicant: Novo Nordisk A/S, Bagsvaerd (DK)

(72) Inventors: Carsten Schau Andersen, Seattle, WA (US); Dave Szakelyhidi, Issaquah, WA (US); Jakob Oest Wielandt, Farum (DK); Matthew William Haave, Seattle, WA (US); Blake Matsuzaki, Bothell, WA (US); Gregory A. Kirkos, Seattle, WA (US); Nikolaj Eusebius Jakobsen, Soeborg (DK)

(73) Assignee: NOVO NORDISK A/S, Bagsvaerd (DK)

( * ) Notice: Subject to any disclaimer, the term of this patent is extended or adjusted under 35 U.S.C. 154(b) by 627 days.

(21) Appl. No.: 16/482,479

(22) PCT Filed: Jan. 22, 2018

(86) PCT No.: PCT/EP2018/051490
§ 371 (c)(1),
(2) Date: Jul. 31, 2019

(87) PCT Pub. No.: WO2018/141571
PCT Pub. Date: Aug. 9, 2018

(65) Prior Publication Data
US 2021/0128841 A1    May 6, 2021

Related U.S. Application Data

(60) Provisional application No. 62/595,856, filed on Dec. 7, 2017, provisional application No. 62/453,132, filed on Feb. 1, 2017.

(30) Foreign Application Priority Data

Feb. 14, 2017  (EP) ..................... 17156143

(51) Int. Cl.
*A61M 5/315*   (2006.01)

(52) U.S. Cl.
CPC .... *A61M 5/31551* (2013.01); *A61M 5/31515* (2013.01); *A61M 5/31568* (2013.01);
(Continued)

(58) Field of Classification Search
CPC ...... A61M 5/31551; A61M 2205/8212; A61M 5/31515; A61M 5/31583; A61M 5/31568;
(Continued)

(56) References Cited

U.S. PATENT DOCUMENTS

| 7,008,399 B2 | 3/2006 | Larsen et al. |
| 7,205,530 B2 | 4/2007 | Jones |

(Continued)

FOREIGN PATENT DOCUMENTS

| CN | 101060872 A | 10/2007 |
| CN | 103458945 A | 12/2013 |

(Continued)

*Primary Examiner* — Theodore J Stigell
(74) *Attorney, Agent, or Firm* — Wesley Nicolas

(57) ABSTRACT

A dosage sensing module for or in a pen drug delivery device and comprising a power source unit, a processor unit and a dosage sensor unit with a first sensor part adapted to be fixed to a part not rotating during dose expelling and comprising a flexible printed circuit board sheet on which a pattern of individual electrical conductive sensor areas are arranged. The sensor unit further comprises a second sensor part adapted to be fixed to the piston rod to follow the rotation thereof during dose expelling. The second sensor part comprises individual structures that together with the conductive sensor areas are adapted to, upon relative rotational movement between the first and second sensor part, provide electrical signals to a processor unit indicative of the relative rotational position between the first and second sensor part.

11 Claims, 20 Drawing Sheets

(52) U.S. Cl.
CPC .............. *A61M 2205/3317* (2013.01); *A61M 2205/3576* (2013.01); *A61M 2205/50* (2013.01); *A61M 2205/8206* (2013.01)

(58) Field of Classification Search
CPC .............. A61M 5/31553; A61M 5/20; A61M 2205/3317; A61M 2205/50; A61M 2205/8206; A61M 2205/52
See application file for complete search history.

(56) References Cited

U.S. PATENT DOCUMENTS

| | | | |
|---|---|---|---|
| 8,348,904 B2* | 1/2013 | Petersen | A61M 5/24 604/207 |
| 11,083,853 B2* | 8/2021 | Grubbe | A61M 5/31553 |
| 11,185,636 B2* | 11/2021 | Mirov | G01D 5/145 |
| 2006/0175427 A1 | 8/2006 | Jonientz et al. | |
| 2008/0188797 A1 | 8/2008 | Enggaard | |
| 2011/0270214 A1* | 11/2011 | Jorgensen | A61M 5/31551 604/207 |
| 2014/0074041 A1 | 3/2014 | Pedersen et al. | |
| 2015/0367077 A1 | 12/2015 | Plambech et al. | |
| 2015/0367079 A1 | 12/2015 | Steel et al. | |
| 2016/0015903 A1* | 1/2016 | Madsen | A61M 5/31568 604/211 |
| 2016/0263327 A1 | 9/2016 | Radmer et al. | |
| 2017/0338864 A1* | 11/2017 | Rolsted | A61M 5/31568 |
| 2021/0283339 A1* | 9/2021 | Frazier | A61M 5/31585 |
| 2021/0290841 A1* | 9/2021 | Katuin | A61M 5/20 |
| 2022/0088317 A1* | 3/2022 | Marcoz | A61M 5/31553 |

FOREIGN PATENT DOCUMENTS

| | | | |
|---|---|---|---|
| CN | 105073165 A | | 11/2015 |
| DE | 102009034897 A1 | | 2/2011 |
| WO | 2006045523 A1 | | 5/2006 |
| WO | 2008113772 A1 | | 9/2008 |
| WO | 2010052275 A2 | | 5/2010 |
| WO | 2010/098927 A1 | | 9/2010 |
| WO | 2014128155 A1 | | 8/2014 |
| WO | WO-2014/128155 | * | 8/2014 |
| WO | 2015185686 A1 | | 12/2015 |
| WO | 2016100202 A2 | | 6/2016 |
| WO | 2016180873 A1 | | 11/2016 |
| WO | 2017114768 A1 | | 7/2017 |

* cited by examiner

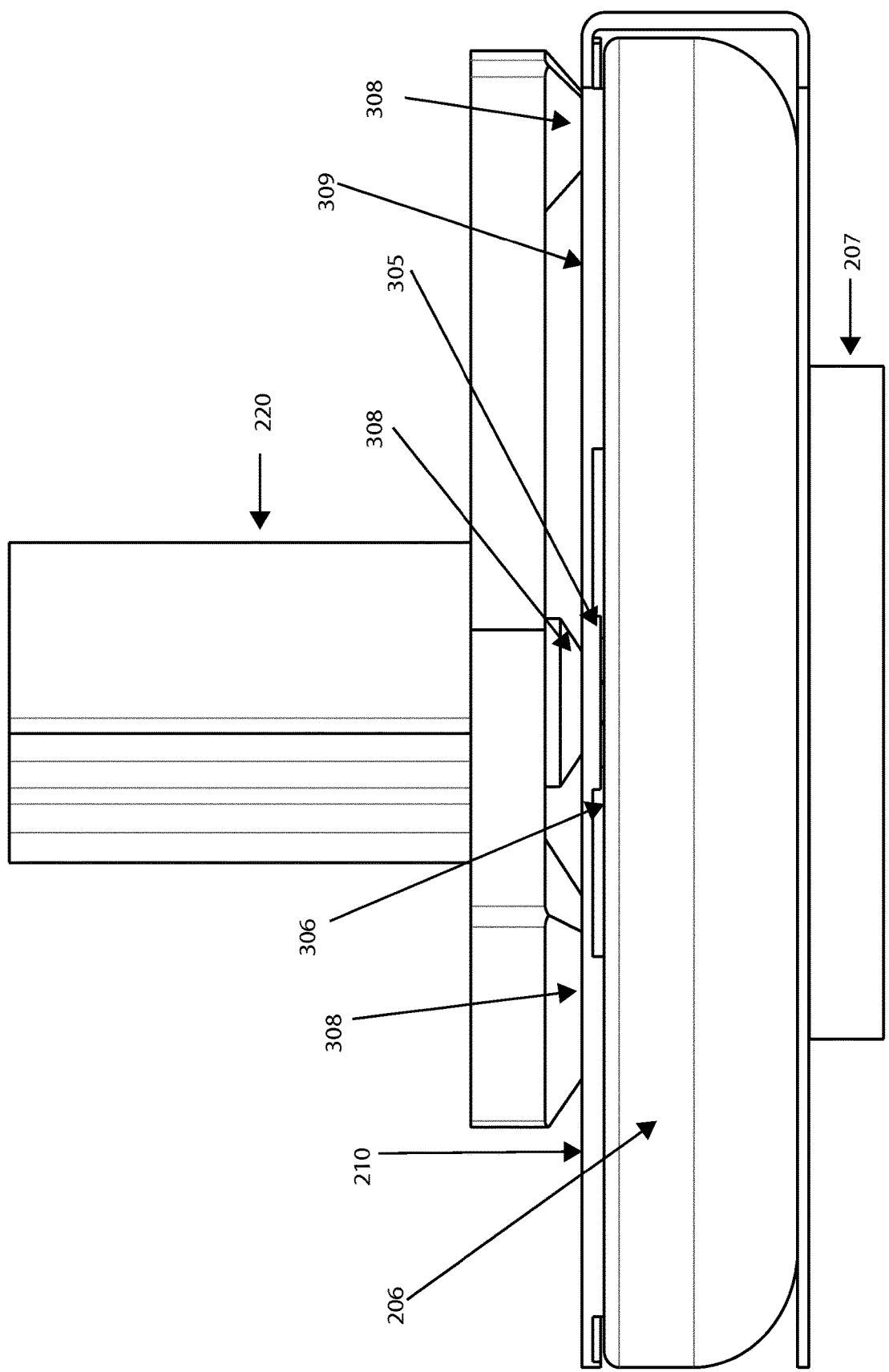

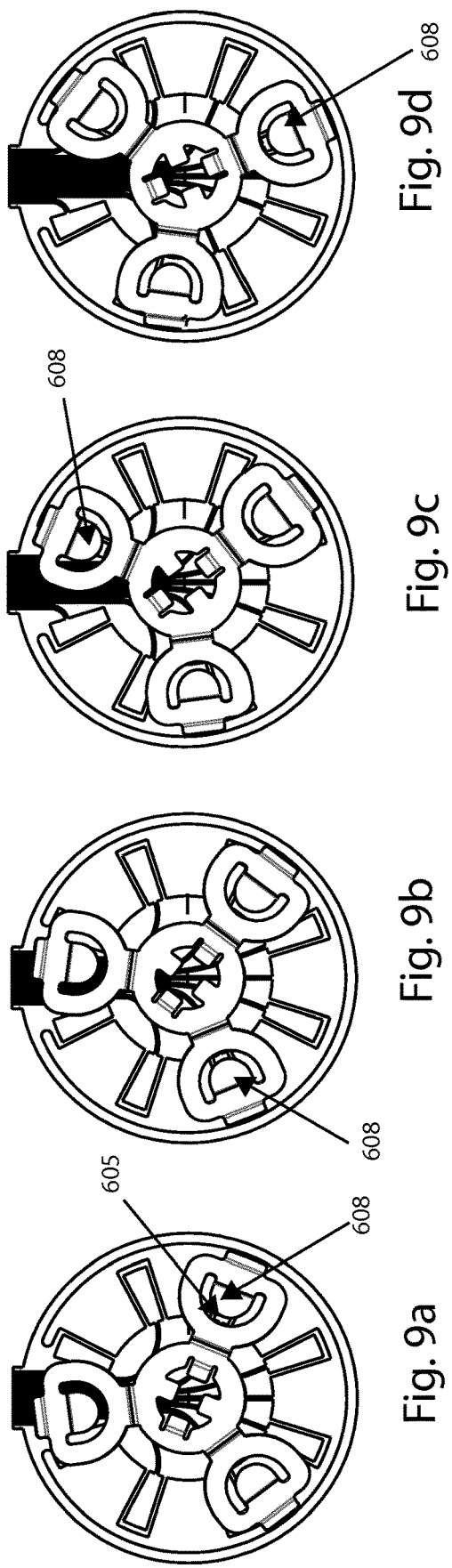
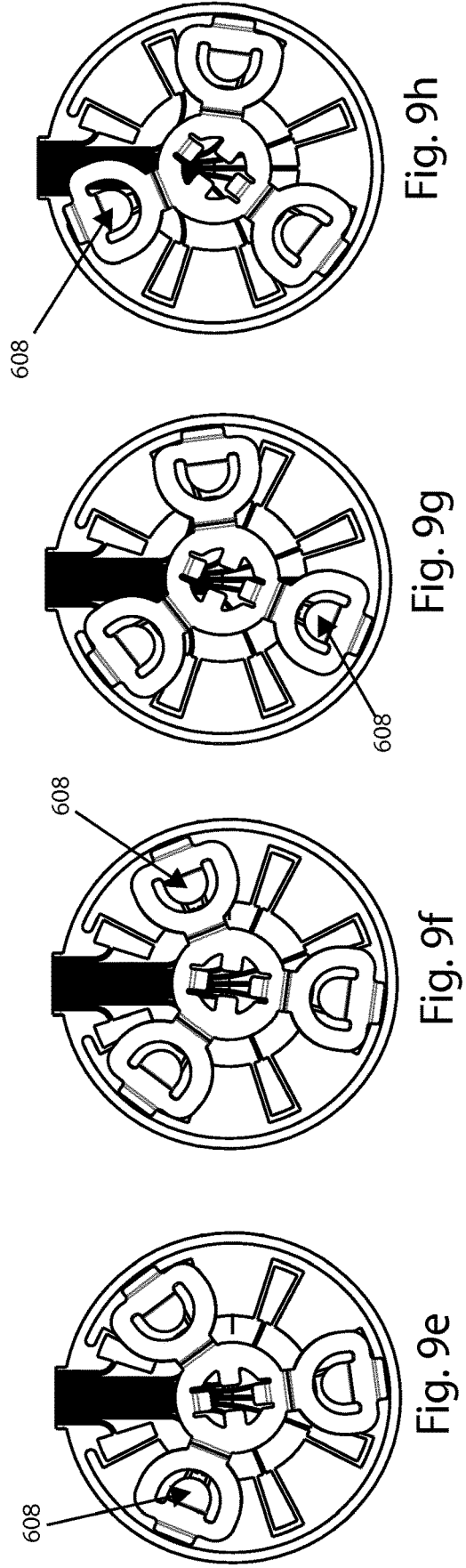

ROTARY DOSAGE SENSING MODULE FOR AND IN A DISPOSABLE PEN DRUG DELIVERY DEVICE

CROSS-REFERENCE TO RELATED APPLICATIONS

This application is a 35 U.S.C. § 371 National Stage application of International Application PCT/EP2018/051490 (published as WO 2018/141571), filed Jan. 22, 2018, which claims priority to European Patent Application 17156143.4, filed Feb. 14, 2017, this application further claims priority under 35 U.S.C. § 119 of U.S. Provisional Applications 62/453,132, filed Feb. 1, 2017 and 62/595,856, filed Dec. 7, 2017, the contents of all above-named applications are incorporated herein by reference.

The present invention relates to a dosage sensing module for and in a pen drug delivery device. In particular, the invention deals with the issue of providing a cost-effective, compact and reliable electronic rotary dose size sensor module for integration into or integrated in a disposable pen drug delivery device, a module that may also be able to communicate dosage data to an external device.

BACKGROUND OF THE INVENTION

Within diabetes performing the necessary insulin injections at the right time and in the right dose size is essential for managing the disease, i.e. compliance with the specified insulin dosage regimen is important to control the blood sugar level and to minimise the risk of hypoglycaemia/hyperglycaemia episodes. In order to make it possible for the patient herself/himself or the HCP to see, if the patient follows the recommended insulin dosage regimen, it is desirable that a log of the dose sizes and the time each dose was taken is kept. It's even better if these data can be transferred to an external source, e.g. mobile phone, server or cloud, for further analysis in order to allow for some guidance to recommended doses and/or adjustments to a present dosage regimen, if needed.

Another objective of dosage data capture is that authorities, payers and providers are increasingly demanding real-world data that demonstrates the efficacy of the insulin drugs in every day. Pharmaceutical drugs are approved for launch in the markets around the globe based on data obtained through clinical trials. However, in clinical trials patients are carefully selected to meet specific criteria and all patients are closely monitored as to their adherence to the treatment regimen. However, this is not the case in real world outside of these clinical trials, where daily lifestyle gets in the way and people are different, doses are missed and other conditions can worsen disease progression. Due to all these variables, the outcomes of treating patient in real world often do not reflect the clinical data on which a given drug was approved for marketing. In view of this it is of high interest to track dose sizes and timing of injections and communicate this data further on to e.g. HCPs. By having this it's possible to follow if patients are in compliance with their diabetes treatment, if patients follow a recommended dosage pattern, and remind them if not and give recommendations to adjustment of dose sizes, if needed. All this for the purpose of optimising the effectiveness of the insulin drug given to the patient and thereby improve their lives as diabetics but also to obtain real-world data to be used for further improvement of the treatment.

One of the most commonly used drug delivery device is a pen injection device. Depending on the type of expelling mechanism embodied in these devices, the expelling mechanism may comprise a spring, which is strained during dose setting and then released to drive a piston rod towards the distal end of the pen to advance a piston in a drug-filled cartridge and thereby expel a dose when a release button is actuated. Alternatively the expelling mechanism may be fully manual. For such types of injection devices, the expelling mechanism often includes a rotating part, e.g. the piston rod and/or a drive tube driving the piston rod, which rotates relative to the piston in the cartridge and/or another non-rotating part in the device. A way to capture expelled dose sizes is to detect number of relative rotations between a rotating part of the expelling mechanism and a non-rotating part, and then based on said relative rotations determine the size of an expelled dose of drug.

Data capturing/monitoring functionality have been proposed for injection devices earlier (see e.g. WO 2010/052275 and U.S. Pat. No. 7,008,399) however most devices are without data capturing. Also durable add-on modules to injection devices have been proposed (see e.g. WO 2010/098927), but as an add-on it requires the users to keep hold of a further device besides their injection pen and blood sugar measurement equipment. It has been also proposed to provide an integrated dose capture unit for a durable pen device (see WO 2014/128155). Further references describe dosage sensing mechanisms, such as US2016/015903 and WO2006/045523.

WO2008/113772 describes a delivery system having container recognition feature to facilitate identification of the specific type of container inserted in the delivery system.

US2016/0263327 refers to a medical device comprising indicator means configured to display information relating to an expelled dose of drug.

A significant part of insulin patients today use disposable pen devices with a prefilled drug cartridge to inject their drug, e.g. insulin or GLP-1 or a combination thereof. However, opposite to durable injection pens, disposable pens with prefilled non-interchangeable drug cartridges are normally made of cheaper components, as their FMC (Full Manufacturing Cost) need to be kept low. For that reason none of the disposable pens in the market today are equipped with integrated electronics like a dose data capturing unit, processor(s), power source(s) etc., which is why only add-on devices for disposable pens exist.

Having regard to the above, it is an object of the present invention to provide a cost-effective, compact and reliable rotary sensor module to be integrated into or being integrated a disposable pen drug delivery device enabling the delivery device to accurately detect dosage data (size and time) without the need for an add-on accessory attached to the pen device.

A further object of the present invention is to provide a cost-effective, compact and reliable rotary sensor module to be integrated into or being integrated a disposable pen drug delivery device enabling the delivery device to accurately detect dosage data (size and time) and further communicate these data to an external device without the need for an add-on accessory attached to the pen device.

An even further object of the invention is to provide a cost-effective, compact and reliable rotary sensor module to be integrated into a disposable pen drug delivery device enabling detection of dosage data (size and time) and communicate these data to an external device and where the integration of the module into an existing device requires minor modifications of the device.

Yet another object of the present invention is to provide a compact, reliable and accurate rotary sensor module to be integrated into or being integrated in an injection device and which adds a minimum of extra torque to drive the dose expelling mechanism.

DESCRIPTION OF THE INVENTION

In the disclosure of the present invention, embodiments and aspects will be described which will address one or more of the above objects or which will address objects apparent from the below disclosure as well as from the description of exemplary embodiments.

According to a first aspect a rotary dosage sensing module is provided for a pen drug delivery device comprising a drug-filled cartridge with a displaceable piston and an outlet and a piston rod to be axially advanced in a direction towards said piston to displace the piston and thereby expel a dosage of drug from the cartridge through the outlet, the piston rod rotating relative to the piston around an axis of rotation (A) during axial movement. The sensing module comprises a power source unit with a (−) and a (+) terminal, a processor unit connected to the (−) and (+) terminals of the power source unit, and a sensor unit comprising; a first sensor part adapted to be directly or indirectly fixed to a part of the delivery device not rotating during dose expelling, the first sensor part comprising a flexible printed circuit board sheet having a first surface on which is disposed a plurality of individual electrical conductive sensor areas arranged in a pattern, some of which being electrically connected to (−) terminal of the power source unit and some of which being connected to the processor unit, and a second sensor part arranged opposite to the first sensor part and adapted to be directly or indirectly fixed to the piston rod to follow the rotation of the piston rod during dose expelling, the second sensor part comprising a plurality of electrically connected contact structures, and wherein the contact structures are connected to the (−) terminal of the power source via those electrically conductive sensor areas that are connected to (−) terminal of the power source, the contact structures being adapted to, upon relative rotational movement between the first and second sensor part, electrically connect different individual electrically conductive sensor areas to the processor unit to thereby close an electrical circuit between the (−) terminal and the processor unit for the different conductive sensor areas, each electrical connection generating an electrical signal to the processor unit being indicative of the rotational position between the first and second sensor part, and wherein the processor unit is adapted to process said signals to determine the amount of relative rotations between the first and second sensor part and thereby calculate the expelled dosage size based on the determined amount of relative rotations.

It should be understood that the conductive sensor areas and contact structures could be connected differently to the power source unit and processor unit and still generating the signals to the processor unit. For example the conductive sensor areas could be connected to the (−) terminal, whereas the contact structures could be connected to the (+) terminal via the processor unit.

By using a flexible printed circuit board (PCB) sheet a very compact module can be obtained compared to using a rigid thicker PCB. Further the electrical connection to the power source unit is easier by use of flexible PCB than using a rigid PCB, and the flexible printed circuit board sheet may e.g. be folded around and adhered to the power source unit and where the first surface of the first sensor part then can be supported by a surface of power source unit. Even further, by use of a flexible PCB sheet, one side of the power source unit can be utilised as a conductive surface area for the sensor unit, as further explained below in connection with one of the embodiments.

The sensor unit is based a rotary sensor principle where the conductive sensor areas in turn are switched in and out of conductive contact with the electrical circuit, a principle providing a very reliable dosage sensing. Further, such as system requires a minimum of power to operate meaning that the size of the power source unit can be limited and thus require little space. Further, as the power requirement to the sensor unit is limited, the cost of the power source can be kept low.

The structures of the second sensor part comprise electrical conductive material providing direct electrical contact to the conductive sensor areas, e.g. as shown in the embodiment of FIGS. 4 and 11. However, as an alternative, the electrical signals from the sensor unit may be generated based on other electrical interaction between the contact structures of the second sensor part and the individual electrical conductive sensor areas. Such interaction could be a capacitive or resistive or inductive interaction.

The module may comprise an electrical switch mechanism to open the electrical circuit to a sensor area after the electrical circuit has been closed and an electrical signal has been received by the processor unit for the sensor area, the switch mechanism being controlled by the processor unit.

The electrical switch mechanism may comprise a pull-up resistor to open the electrical circuit to a sensor area a predefined time after the electrical circuit has been closed and an electrical signal has been received by the processor unit for the sensor area, the pull-up resistor being controlled by the processor unit. This will effectively save power as the sensor areas don't need to be powered up all the time to monitor sensor transitions.

However, a detection of the next sensor transition for this specific sensor area will not be detected as the electrical circuit is open by the pull-up resistor. A way of reducing this problem is to implement an intelligent control of the pull-up resistors. Initially, only pull-up resistors for all open electrical circuits are activated. When a sensor transition is detected all pull-up resistors are activated, allowing software in the processor unit to detect all sensor transitions and a timer is started. Every time a sensor transition is detected, the timer is reset to its original value, and when the timer times out, the system reverts to only having the pull-up resistors for open electrical circuits activated. The sensor will consume power during and shortly after a detected transition but will zero-power when static.

The individual electrically conductive sensor areas may be distributed circumferentially around a centre axis (B) of the first sensor part and where the module further comprises a centering element with a bearing cup part having a centre axis (C) and arranged in relation to the first sensor part such that said centre axis (C) coincides with the centre axis (B), the bearing cup part being adapted to maintain a distal tip part of the piston rod in a position, during dose expelling, where the centre axis (A) is coinciding with the centre axis (B).

By providing the centering element with a bearing cup part, there is completely alignment between the first and second sensor part, which is essential for the rotary sensor to detect every transition accurately. If there is only a minor misalignment, then the contact structures of the second sensor part may not engage the sensor areas of the first sensor part properly but jump some connections and not generate a signal. Thereby the readout from the rotary sensor will be inaccurate resulting in a wrong determination by the processor unit of the number of relative rotations and thus wrong dose size calculation. Even very small deviations in centering can result in an incorrect measurement of dose size.

Furthermore, by having the centering element with the bearing cup part located exactly at the center of the axis of rotation, the torque exerted to rotate the second sensor part in relation to the first sensor part is minimised leading to a minimal additional torque required to drive the expelling mechanism in the injection device. Without this centering element a larger torque would be needed, which would lead to a larger spring in the dose expelling mechanism of an automatic pen or a larger injection force to be applied manually by the user for a manual pen.

In an exemplary embodiment the second sensor part is adapted to form part of the distal tip part of the piston rod. In that case the bearing cup part is adapted to receive and maintain the part of the second sensor part forming the distal tip part in a position, during dose expelling, where the centre axis (A) is coinciding with the centre axis (B).

To optimise the centering of the piston rod and thereby second sensor part in relation to the first sensor part and to minimise the torque needed to rotate the two parts in relation to each other, the bearing cup part preferably has a rotationally symmetrical shape around its centre axis (C).

The cross-sectional shape of the bearing cup part, seen parallel to the centre axis (C), may vary in form depending on desired level of play between the distal part of the piston rod and the cup part. The cross-sectional shape may e.g. be substantially V- or U- or trapezoidal- or square-shaped.

The centering element and first sensor part are arranged in a fixed mutual position, such that their respective centre axis' coincide. To provide this mutual fixed position, the centering element may either be soldered or riveted or glued to the first sensor part, or it may be formed integrally with the first sensor part.

In an exemplary embodiment the bearing cup part is made of electrically conductive material and connected to the (−) terminal of the power source unit and wherein the second sensor part, when maintained in the bearing cup part, is electrically connected to the bearing cup part. This would allow for an electrical ground signal to be passed to the second sensor part. For further details on such an embodiment reference is made to FIGS. 12*b* and 13*b* and associated description.

The number of individual electrical conductive sensor areas and contact structures may vary depending on the specific use (drug, pen etc.) and desired code pattern, e.g. a Gray code or quadrature code pattern. The number of sensor areas may e.g. be 3 or 4 or 6 or 8 or even more such as 24 or 48 or 72, and the number of contact structures may be 2 or 3 or 4 or even more.

The conductive sensor areas may be provided either by disposing, e.g. by printing, layer(s) of conductive material on the flexible printed circuit board sheet in specific patterns or by first disposing layer(s) of conductive material on the sheet and afterwards removing material to form the sensor areas. The conductive material may be any suitable conductive material, such as silver, copper, carbon or gold and the thickness of the layer(s) may be e.g. 0.01-0.05 mm, but it can be more or less than that.

The first surface on which the conductive sensor areas are arranged may extend substantially perpendicular to or parallel with said axis of rotation (A).

The flexible printed circuit board sheet may be a thin foil with a thickness of e.g. 0.05-0.1 mm meaning it easily can be folded as needed, which allows for a very compact construction of the module, as depicted in the examples in the figures.

Further, as the flexible printed circuit board sheet can be mass produced, e.g. in processes like a "role-on-role" process allowing thousands of individual sheets to be printed fast, a very low cost per sheet can be achieved.

The power source unit may be a standard battery, e.g. a coin cell, however alternatively it may also be a power source disposed on the flexible PCB sheet in the form of a printed battery allowing for an even more compact construction of the module. As the processor unit preferably should be able to keep track of time, e.g. through a real time clock unit, the power source unit may be adapted to supply a low "sleep current" to the processor unit in order to continuously power the clock unit.

The sensor unit may be adapted to be switched from an inactive (off) state into an active (on) state by an initial first relative axial and/or rotational movement between the first and second sensor part. For example the sensor unit may be in "off" mode prior to dose expelling and then be switched "on" just before dose expelling, e.g. during activating the dose expelling mechanism of the pen. By activating the sensor unit just before dose expelling, the module will be able to determine the exact relative position between the first and second sensor part before the two parts start rotating relative to each other.

The processor unit may be in the form of a microprocessor, microcontroller or CPU, which may be of a general purpose design or be specifically designed for the actual device. The processor unit is adapted to, based on the signals received from the dosage sensor unit indicative of the relative rotational position between the first and second sensor part, to calculate a corresponding expelled dose and store this data, including the time for when each dosage of drug was taken. However, instead of the processor unit calculates the actual dose amount, the stored data may be in the form of no. of rotation data only, this allowing a receiving external unit, e.g. a smartphone or PC, to calculate the actual drug dose amounts based on supplied information in respect of the type of drug, type of cartridge, and type of device.

The module preferably comprises a communication unit to wirelessly communicate the stored data to an external device. The communication unit may be disposed on said flexible printed circuit board sheet. The communication unit may be adapted to communicate, via communication technologies like NFC, Bluetooth, BLE (Bluetooth Low Energy), Wi-Fi, ZigBee, ZigFox, LoRa, GSM, Narrow Band or any other wireless communication technology, the dosage data to any unit, such as a smartphone, server or cloud.

Most existing piston rods of the type which rotates during expelling of a dose comprise a distal piston-engaging foot or washer allowing the piston rod to freely rotate during out-dosing while ensuring non-rotational engagement with the elastomeric piston. The sensor module may substitute this piston rod foot, i.e. besides providing dosage sensing it provides the same function as a piston rod foot or washer. As the size of the module can be of the same size as a piston rod foot or washer an integration of the module into a pen will require very limited modifications of the pen. In such embodiment, the module is positioned in between the piston and piston rod with the first sensor part engaging the piston such that no rotation between the piston and the first sensor part is possible and with the second sensor part engaging an end portion of the piston rod such that no rotation between the second sensor part and piston rod is possible, and wherein the module may be adapted to be moved axially into the cartridge corresponding to the axial movement of the piston and piston rod during expelling of a dose. The piston rod will during expelling of a dose exerts a distally directed force on the module, the force being transferred to the piston by the module. The power source unit of the module may constitute the load bearing part transferring the force from the piston rod to the piston.

In another embodiment, the module is adapted to be integrated into the pen in an end opposite to the end containing the cartridge, i.e. in the end of the pen normally containing the dose setting and dose activation mechanism. A detailed description of such integration is provided in connection with FIG. 7.

It should also be understood that the module may be positioned oppositely in the pen, such that the first sensor part is rotating during dose expelling and the second sensor part is not rotating during dose expelling. For example can the first sensor part engage directly or indirectly with the piston rod to follow the rotation thereof and the second sensor part can engage directly or indirectly the piston.

Adapted for the specific purpose of being arranged in either end of the pen as described above, the module may have an effective diameter of less than 20 mm, less than 15 mm, less than 10 mm or less than 8 mm, and a height of less than 10 mm, less than 8 mm, less than 6 mm or less than 4 mm.

According to another aspect, a rotary dosage sensing module is provided for a pen drug delivery device comprising a drug-filled cartridge with a displaceable piston and an outlet and a piston rod to be axially advanced in a direction towards said piston to displace the piston and thereby expel a dosage of drug from the cartridge through the outlet, the piston rod rotating relative to the piston around an axis of rotation (A) during axial movement. The module comprises a power source unit with a (−) and a (+) terminal, a processor unit connected to the (−) and (+) terminals of the power source unit, and a sensor unit comprising; a first sensor part adapted to be directly or indirectly fixed to a part of the delivery device not rotating during dose expelling, the first sensor part comprising a flexible printed circuit board sheet having a first surface on which is disposed a plurality of individual electrical conductive sensor areas arranged in a pattern, some of which being electrically connected to (−) terminal of the power source unit and some of which being connected to the processor unit, and a second sensor part arranged opposite to the first sensor part and adapted to be directly or indirectly fixed to the piston rod to follow the rotation of the piston rod during dose expelling, the second sensor part comprising a plurality of contact structures, and wherein the contact structures are adapted to, upon relative rotational movement between the first and second sensor part, close an electrical circuit between the (−) terminal and the processor unit for the different conductive sensor area, each electrical connection generating an electrical signal to the processor unit being indicative of the rotational position between the first and second sensor part, and wherein the processor unit is adapted to process said signals to determine the amount of relative rotations between the first and second sensor part and thereby calculate the expelled dosage size based on the determined amount of relative rotations.

In one embodiment, the dosage sensor unit further comprises a second surface area arranged perpendicularly relative to the axis of rotation and axially offset to the first surface of the first sensor part with the individual electrical conductive sensor areas and wherein an electric conductive material connected to the (−) terminal forms the second surface area, and wherein a spacer is arranged to provide axial spacing between the first and second surface areas but to enable individual sub-areas of the first surface area carrying the individual electrical conductive sensor areas to be deflected to bring the different individual electrical conductive sensor areas into electrical contact with the second surface area when the first surface area is acted upon by the individual contact structures of the second sensor part to close the electrical circuit between the (−) terminal and the processor unit for the different sensor areas. A conductive surface area of the power source unit may constitute said second surface area.

The spacer may comprise any kind of material in the state of solid or liquid or gas.

According to another aspect of the invention, a module as described above is provided in combination with a pen drug delivery device comprising a housing, a drug-filled non-interchangeable cartridge with a displaceable piston and an outlet and a piston rod to be advanced in a direction towards said piston to displace the piston and thereby expel a dosage of drug from the cartridge through the outlet, the piston rod rotating relative to the piston and housing during axial movement, and wherein the first sensor part of the module is directly or indirectly engaged with the housing such that no relative rotation between the housing and the first sensor part is possible, and the second sensor part of the module is directly or indirectly engaged with the piston rod such that no relative rotation between the piston rod and the second sensor part is possible.

According to an even further aspect of the invention, a rotary dosage sensing module is provided for sensing dosage sizes in a pen drug delivery device comprising a drug-filled cartridge with a displaceable piston and an outlet, and dose expelling means with a piston rod rotating relative to said piston during dose expelling to drive and displace said piston towards said outlet and thereby expel a dosage of drug through the outlet. The sensor module defines an axis of rotation and comprises a power source unit with a (+) and a (−) terminal, a processor unit connected to the (−) and (+) terminal, and a sensor unit comprising a first cylindrical-formed rotary sensor part having a plurality of individual electrically conductive sensor areas arranged in a pattern around the cylindrical surface extending parallel to the axis of rotation, each sensor area being connected to the (−) terminal of the power source unit. Said first rotary sensor part being adapted to be indirectly or directly fixed to the piston rod to follow the rotation thereof during dose expelling. The sensor module further comprises a second stationary sensor part adapted to be directly or indirectly fixed to a part of the delivery device not rotating during dose expelling, the stationary sensor part comprising a flexible printed circuit board sheet having a first surface on which is disposed a plurality of contact structures arranged in a pattern, each being electrically connected to said processor unit, and wherein the rotary and stationary sensor part are arranged co-axially and at least partially inside each other such that the contact structures are adapted to, upon relative rotational movement between the first and second sensor part, electrically connect different individual electrically conductive sensor areas to the processor unit to thereby close an electrical circuit between the (−) terminal and the processor unit for the specific conductive sensor area, each electrical connection generating an electrical signal to the processor unit being indicative of the rotational position between the first and second sensor part, and wherein the processor unit is adapted to process said signals to determine the amount of relative rotations between the first and second sensor part and thereby calculate the expelled dosage size based on the determined amount of relative rotations.

According to a further aspect of the invention a dosage sensing module is provided for a pen drug delivery device comprising a drug-filled cartridge with a displaceable piston and an outlet and a piston rod to be advanced in a direction towards said piston to displace the piston and thereby expel a dosage of drug from the cartridge through the outlet, the piston rod rotating relative to the piston during axial movement, said module comprising; a dosage sensor unit comprising a first sensor part adapted to be directly or indirectly fixed to a part of the delivery device not rotating during dose expelling, the first sensor part having a plurality of individual electrical conductive sensor areas, a second sensor part adapted to be directly or indirectly fixed to the piston rod to follow the rotation thereof during dose expelling, the first and second sensor part being rotatable relative to each other and arranged axially offset to each other and perpendicularly relative to the axis of rotation, the module further comprising a processor unit, a power source unit adapted to power at least the dosage sensor unit and processor unit, and a flexible printed circuit board sheet on which is disposed said plurality of individual electrical conductive sensor areas and electrical conductor(s) for providing electrical connections between the plurality of individual electrical conductive sensor areas, the processor unit and power source unit, and wherein said second sensor part of the sensor unit comprises individual structures that together with said individual electrical conductive sensor areas are adapted to, upon relative rotational movement between the first and second sensor part, provide electrical signals being indicative of the relative rotational position between the first and second sensor part, and wherein the processor unit is adapted to receive and process said signals to determine the amount of relative rotations.

The rotation preventing engagement between the first sensor and the piston or housing and between the second sensor part and the piston rod may be based on any suitable friction- or form-based engagement. In particular, the engagement to the elastomeric piston could be based on gluing or by means of protrusions on the module either penetrating into the piston or providing sufficient friction to prevent relative rotation between the piston and module.

Based on the above, a cost-effective, reliable and compact module is provided enabling the delivery device to accurately detect dosage data (size and time). and further communicate these data to an external device without the need for an add-on accessory attached to the pen device. Further, a module is provided where the integration into the device requires very little modification of the device.

Though the module due to its compact, inexpensive construction is intended for use in a disposable device, it should be understood that it also can be implemented in a durable and more expensive pen drug delivery device.

As used herein, the term "drug" is meant to encompass medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiment reference will be made to the use of insulin and GLP-1 containing drugs, this including analogues thereof as well as combinations with one or more other drugs.

BRIEF DESCRIPTION OF THE DRAWINGS

In the following the invention will be further described with reference to the drawings, wherein FIGS. 3a-c show views of the module as arranged in the pen in FIG. 2, FIGS. 9a-h show the connection sequence of the module shown in FIGS. 6a-c and 7, FIGS. 10a-h show am example of a connection sequence of a module according to the invention.

DETAILED DESCRIPTION OF THE DRAWINGS

Figure 1:
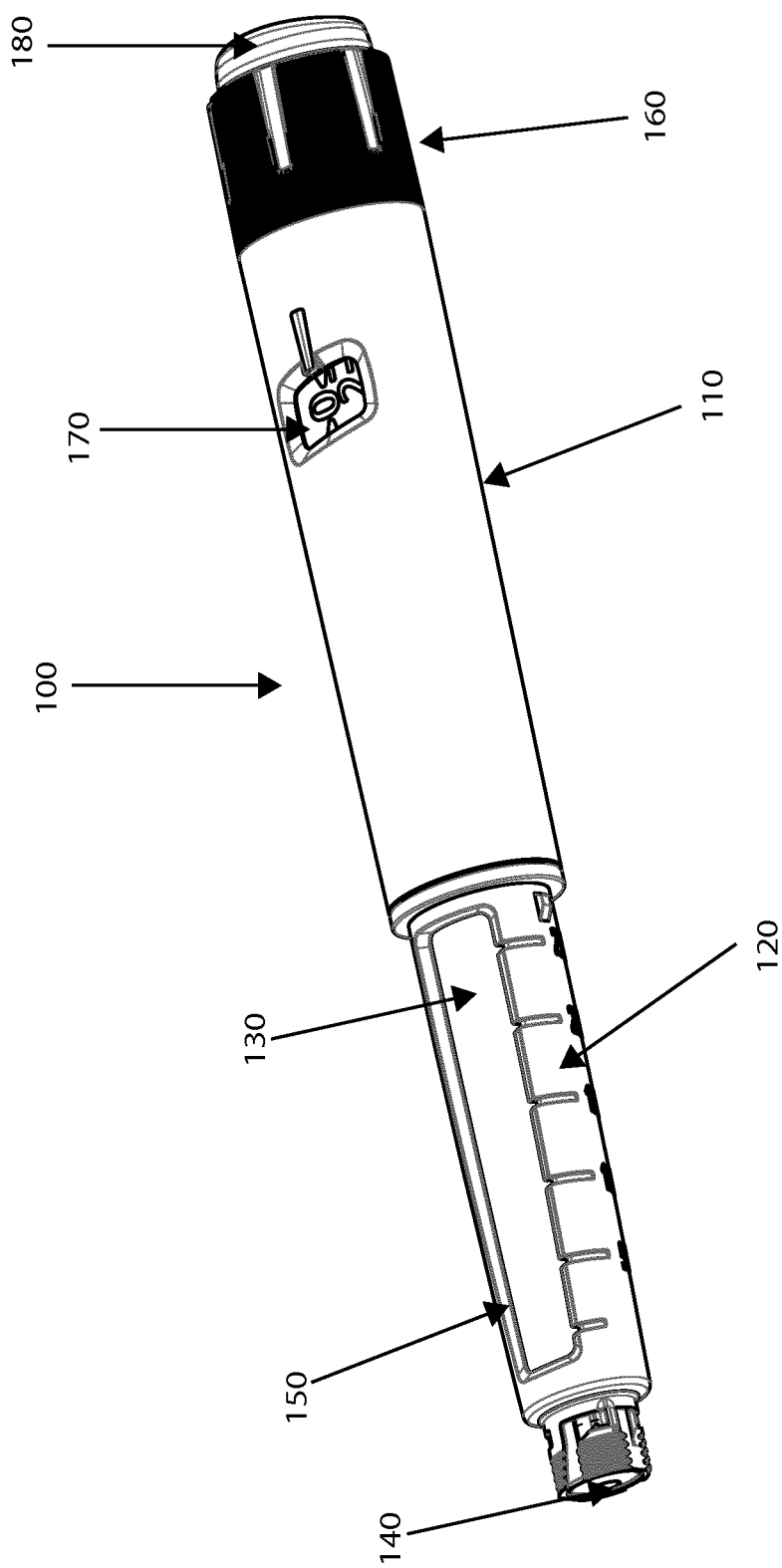
FIG. 1 shows a disposable pen drug delivery device with a drug cartridge.

Referring to FIG. 1 a disposable pen drug delivery device 100 is shown with which the module according to the invention may be used. The device may represent a generic drug delivery device, however the one shown in FIG. 1 is a FlexTouch® prefilled pen drug delivery device sold by Novo Nordisk A/S. This pen is a spring driven pen and is described in detail e.g. in patent application WO2014/161952, the disclosure of which is hereby incorporated by reference.

More specifically, the pen device comprises a main part having a proximal body or drive assembly portion with a housing 110 in which a drug expelling mechanism is arranged or integrated, and a distal cartridge holder portion 120 holding a drug-filled transparent cartridge 130 having a displaceable piston (not shown) and distal needle-penetrable septum 140. The cartridge holder has openings 150 allowing a portion of the cartridge to be inspected. The cartridge may for example contain an insulin, GLP-1 or growth hormone formulation. A proximal-most rotatable dose ring member 160 serves to manually set a desired dose of drug shown in display window 170 and which can then be expelled when the release button 180 is actuated.

Depending on the type of expelling mechanism embodied in the drug delivery device, the expelling mechanism may comprise a spring, as in the pen shown in FIG. 1, which is strained during dose setting and then released to drive a piston rod towards the distal end of the pen to advance a piston in the cartridge and thereby expel a dose when the release button is actuated. Alternatively the expelling mechanism may be fully manual.

Figure 2:
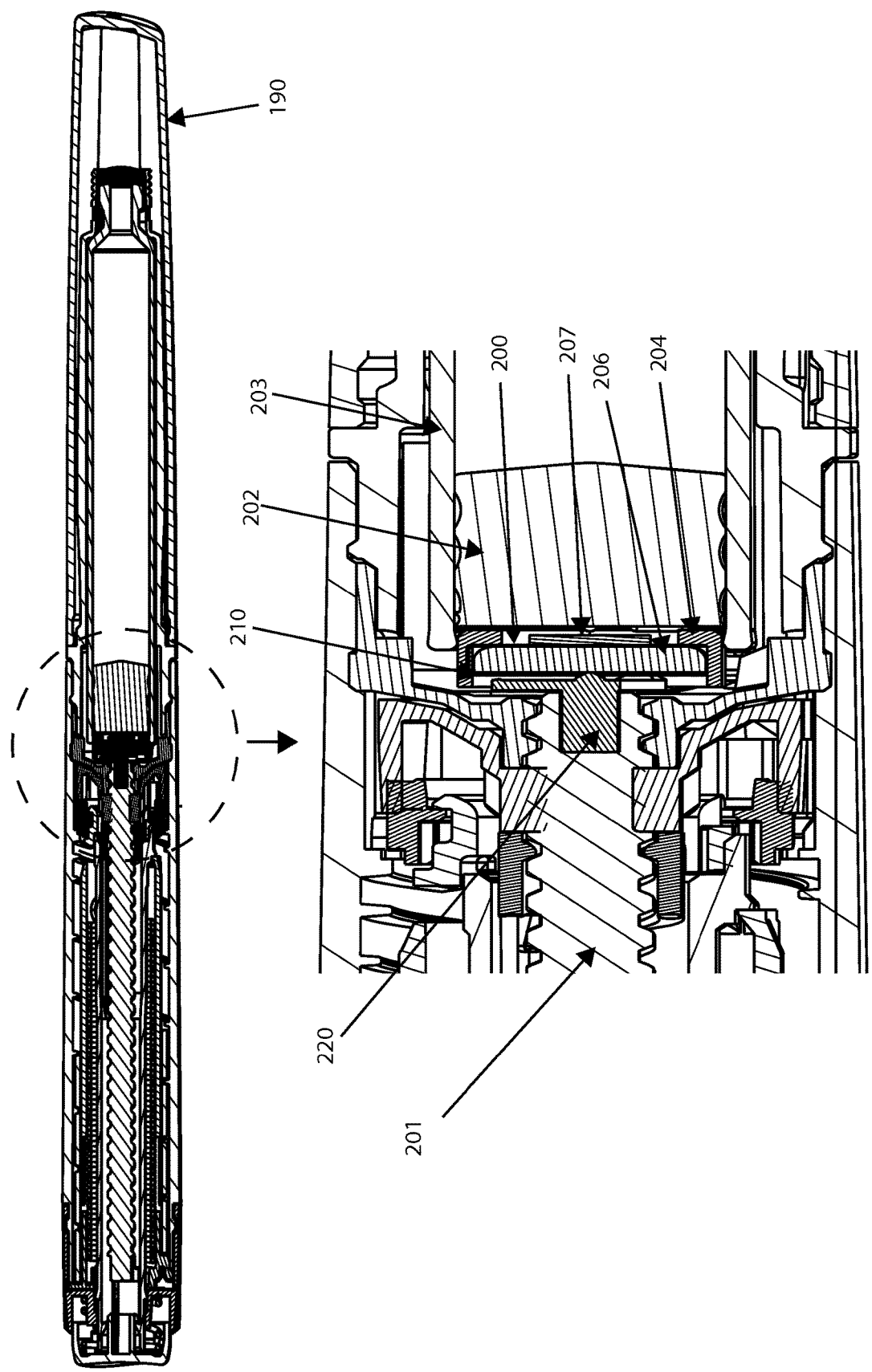
FIG. 2 shows a cross sectional view of the pen shown in FIG. 1 with an embodiment of a sensor module according to the invention.

FIG. 2 shows a cross sectional view of the pen shown in FIG. 1 (though the pen here also includes a cap part 190) and wherein a module according to the invention is arranged. The module (shown in detail in FIGS. 3*a*-*c*) is arranged between the piston rod 201 and the piston 202 of the cartridge 203, and where the first sensor part 210 of a sensor unit of the module is rotationally locked to the piston 202 in the cartridge via the housing 204.

The second sensor part 220 (the "wiper") is rotationally locked to a tip part of the piston rod 201. As the first 210 and second sensor part 220 can rotate relative to the each other and as the piston 202 doesn't rotate during dose expelling, a rotational movement of the piston rod 201 during dose expelling will cause the second sensor part 220 to rotate relative to the first sensor part 210.

Figure 3A:
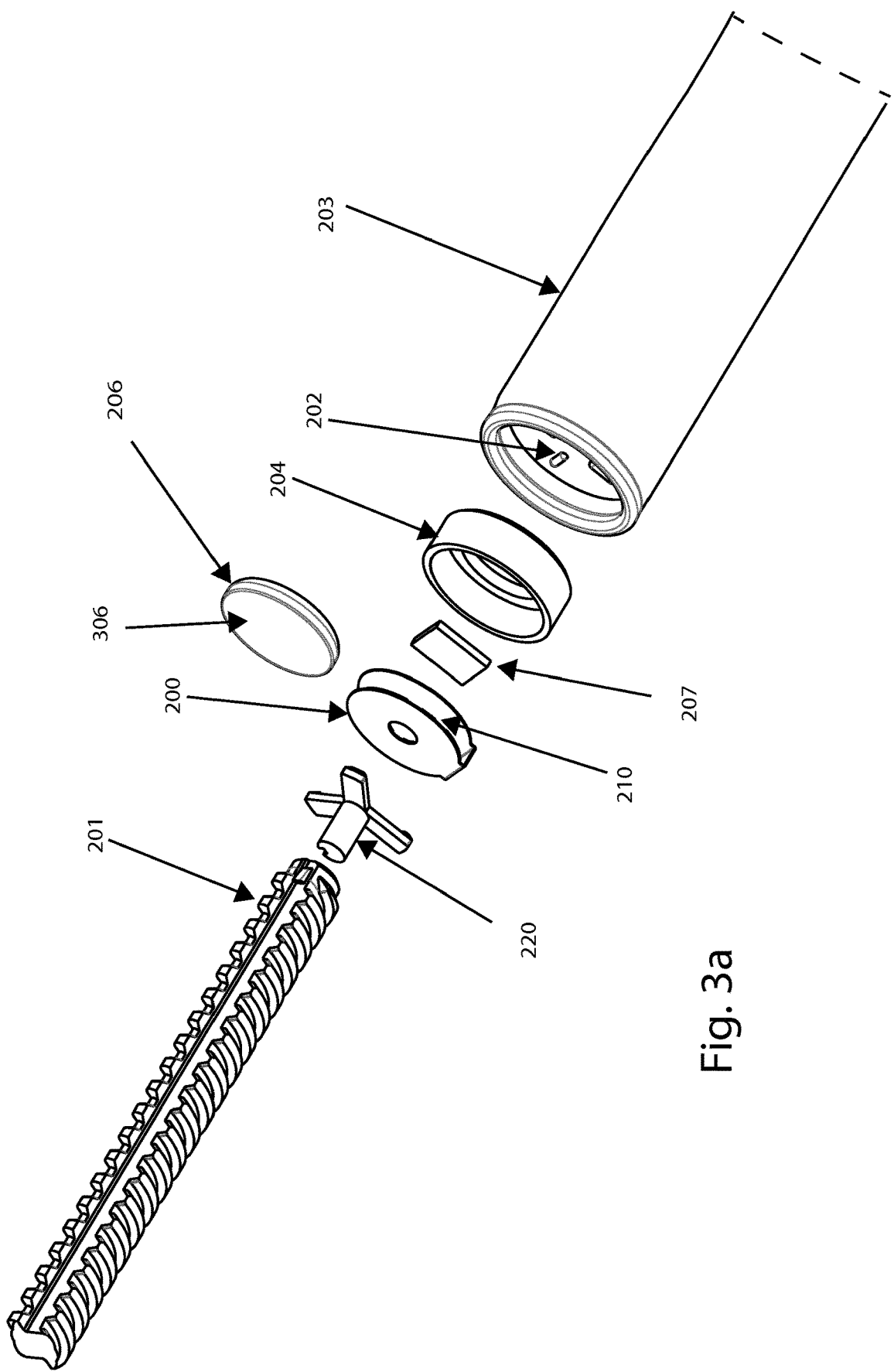
Figure 3B:
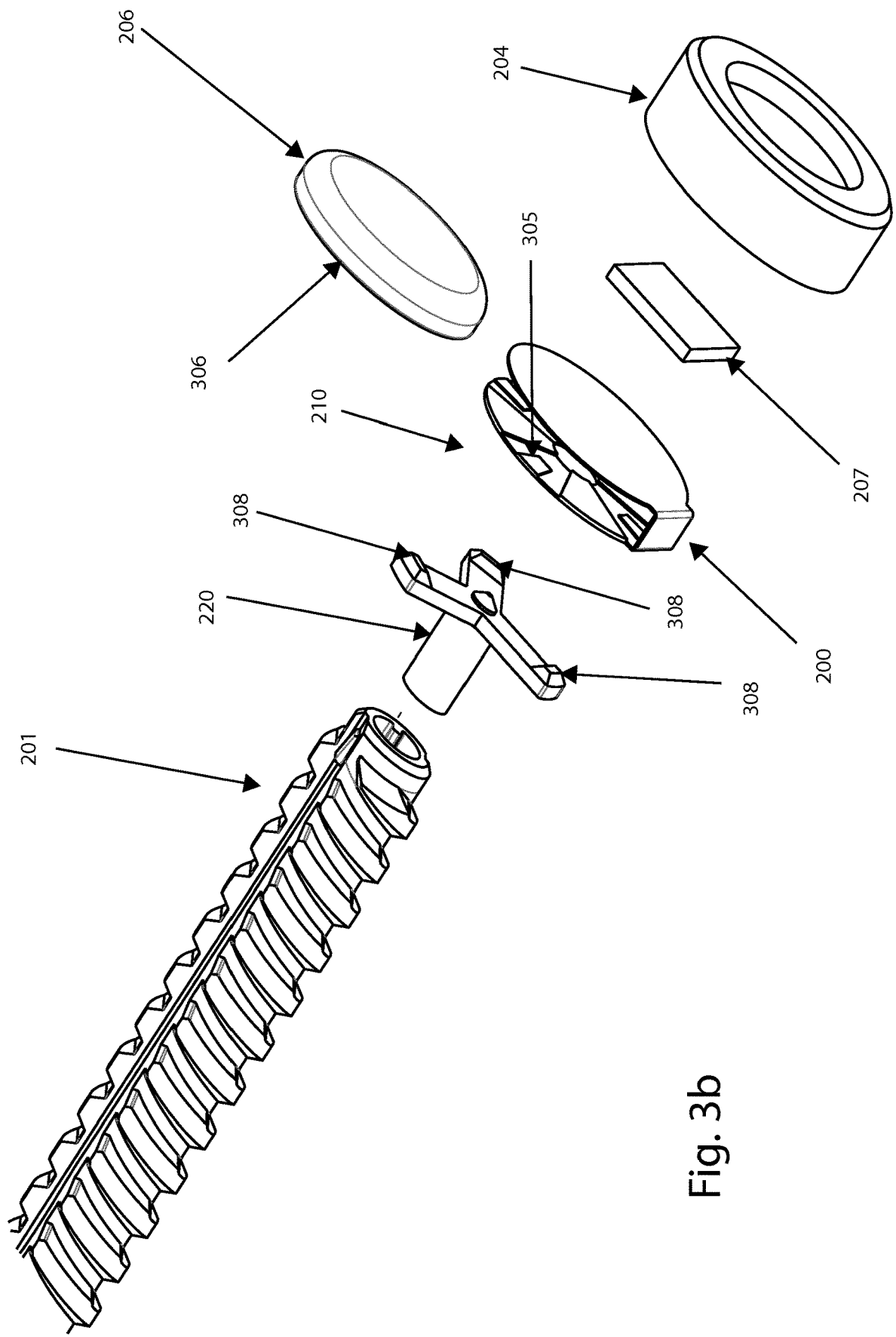

In FIGS. 3*a*-*c* is shown the module also shown in FIG. 2 with the flexible printed circuit board sheet 200 folded around the battery 206 in the form of a cell coin battery, i.e. the battery is meant to be positioned in between the two layers of the folded sheet 200, as shown in FIG. 3*c*. The sheet may be adhered to both side of the battery. One advantage of this build up of the module is that the battery is used as the main load bearing part of the module, when the piston rod exert a force on the module to axially advance the piston in the cartridge to expel a dose of drug.

The second sensor part 220 has individual contact structures 308 in the form of three flexible arms adapted to deflect the different conductive sensor areas 305 of the first sensor part 210 into contact with a surface 306 of the battery (e.g. the (−) terminal) and thereby close the electrical circuit between the (−) terminal and processor unit 207 to provide an electrical signal, when the first 210 and second sensor part 220 rotate relative to each other.

The first sensor part 210, when placed in the pen, will via the housing part 204 be in a non-rotational engagement with the piston 202 of the cartridge 203.

Conductor(s) on the flexible PCB sheet may provide connection allowing the battery 206 to deliver a continuous low "sleep current" to the processor unit 207 in order for the processor unit to keep track of time however it may first be activated when the module is used for the first time.

The flexible printed circuit board sheet may also comprise means for wireless communication (see e.g. FIG. 6*b*) of data to an external device, e.g. an antenna may be disposed on the sheet.

FIG. 3*c* shows a side-view of the assembled module. When the first sensor part 210 and second sensor part 220 rotate relative to each other during dose expelling, when the module is arranged in the pen, the individual structures 308 of the second sensor part will deflect the conductive sensor areas 305 of the first sensor part into connection with the surface 306 of the battery, the surface being either the (−) or (+) terminal of the cell coin battery. In the figure, the sensor area 305 shown has not been deflected into connection yet, as there is a small space between the sensor area 305 and the surface 306, however it will be deflected into connection when a structure 308 overlaps the sensor area 305 upon relative rotation between the first and second sensor part.

The sensor areas 305 and the structures 308 are configured to create a pattern of contact positions indicative of a rotational position between the first and second sensor part, and the processor unit 207 can then process the electrical signals received indicative of the relative rotational position between the first and second sensor part to determine the amount of relative rotation and based thereon calculate a corresponding expelled dose and store this data.

Figure 4:
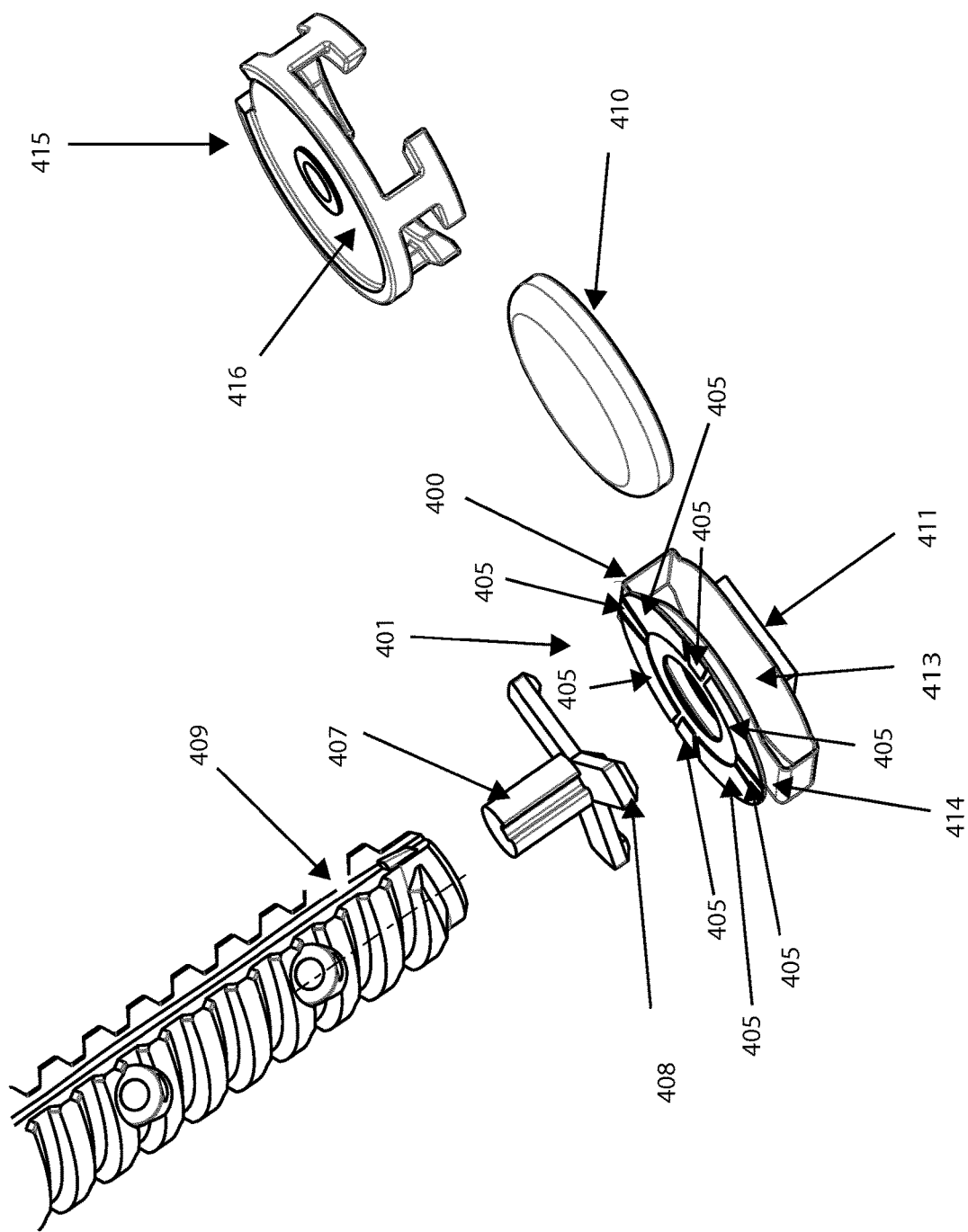
FIG. 4 shows another embodiment of the module according to the invention.

In another embodiment shown in FIG. 4, electrically connected contact structures 408 of the second sensor part 407 are adapted to connect conductively directly to the plurality of individual electrically conductive sensor areas 405 of the first sensor part 401 upon relative rotation between the first and second sensor part. An advantage of this embodiment is that the torque applied on the structures of second sensor part is low as the structures don't have to deflect the sensor areas 405.

The battery 410 is intended to be positioned in the space 413 in the folded flexible printed circuit board sheet 400. A housing 415 is provided to house the flexible printed circuit board sheet 400, the battery 410 and the processor unit 411, the housing being arranged such that the surface 416 is positioned in the space 414 and thus supports the first surface of the first sensor part 401 underneath. The small conductive sensor areas of the first sensor part will be connected to the processor unit and the large sensor areas will be connected to (−) terminal of the power battery 410. In this embodiment the second sensor part may be connected to the (−) terminal but not necessarily.

The second sensor part 407 is adapted to engage the piston rod 409 such that no rotation between the second sensor part and piston rod is not possible, and the housing 415, including the flexible printed circuit board sheet 400, battery 410 and processor unit 411, is adapted to engage the piston of the drug cartridge (not shown), such that no rotation between the housing and thus first sensor part 401 is possible.

When the first 410 and second sensor part 407 rotate relative to each other the contact structures 408 electrically connect the different conductive sensor areas 405 of the first sensor part and thereby close the electrical circuit between the (−) terminal and processor unit 411 to provide an electrical signal to the processor unit being indicative of the rotational position between the first and second sensor part, and the processor unit is adapted to process the signals to determine the amount of relative rotations and thereby calculate the amount of expelled dosage size.

Figure 5:
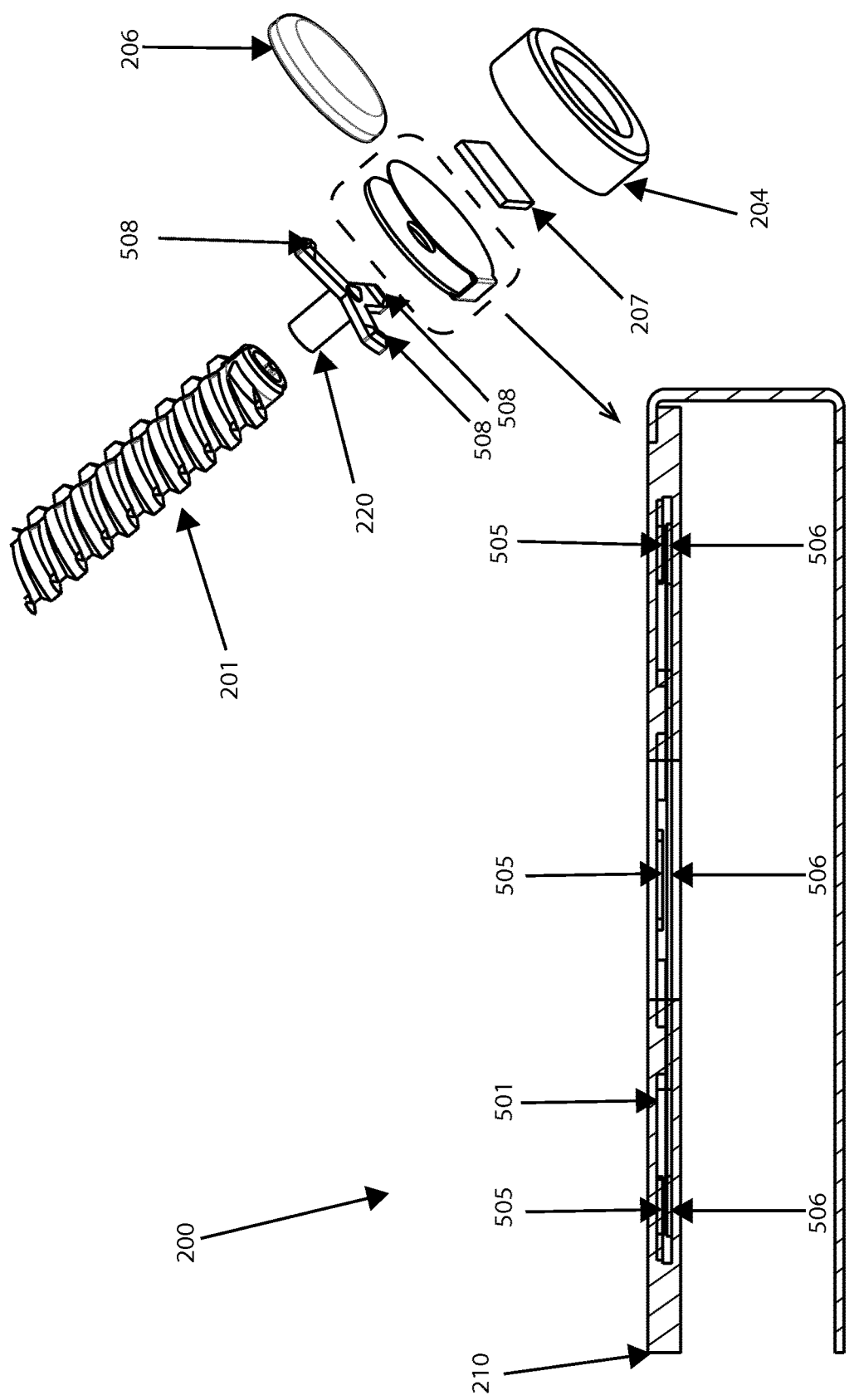
FIG. 5 shows a third embodiment of the module according to the invention.

FIG. 5 shows another embodiment of the module according to the invention. As can be seen in the detailed cross-sectional view of the flexible printed circuit board sheet 200, the first sensor part 210 of the dosage sensor unit has a first surface 501 on which the individually electrically conductive sensor areas 505 are disposed on. A second surface area 506 is arranged axially offset to the areas 505 and perpendicularly relative to the axis of rotation of the second sensor part 220, and where electric conductive material forms the second surface area 506. As the structures 508 upon rotation of the second sensor part 220 overlaps the individually electrically conductive sensor areas 505, the structures will deflect the sensor areas 505 into conductive electrical connection with the second surface area 506 to close the electrical circuit and provide the signals to the processor unit.

Figure 6A:
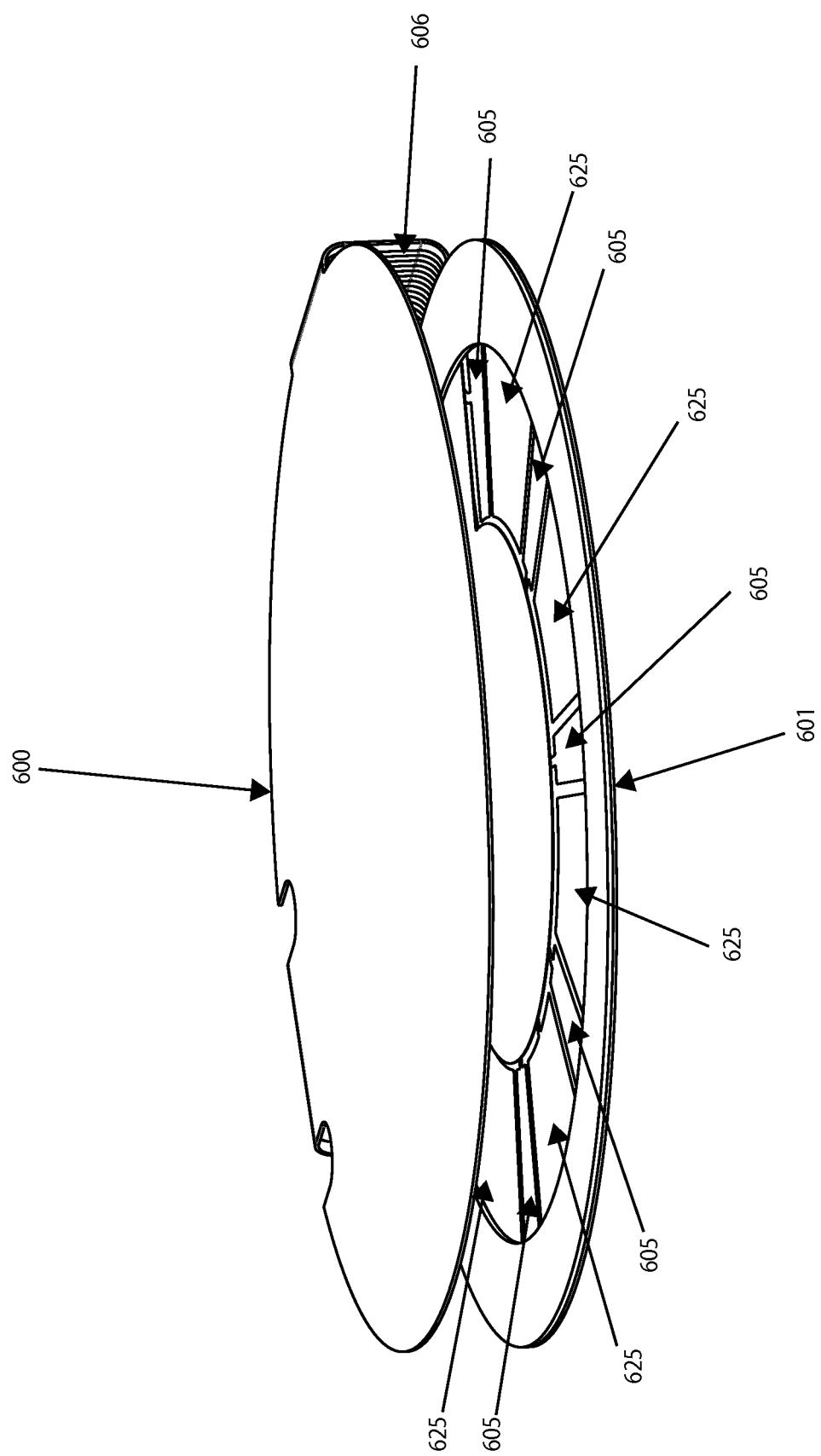
FIGS. 6a-c show fourth embodiment of module according to the invention.
Figure 6B:
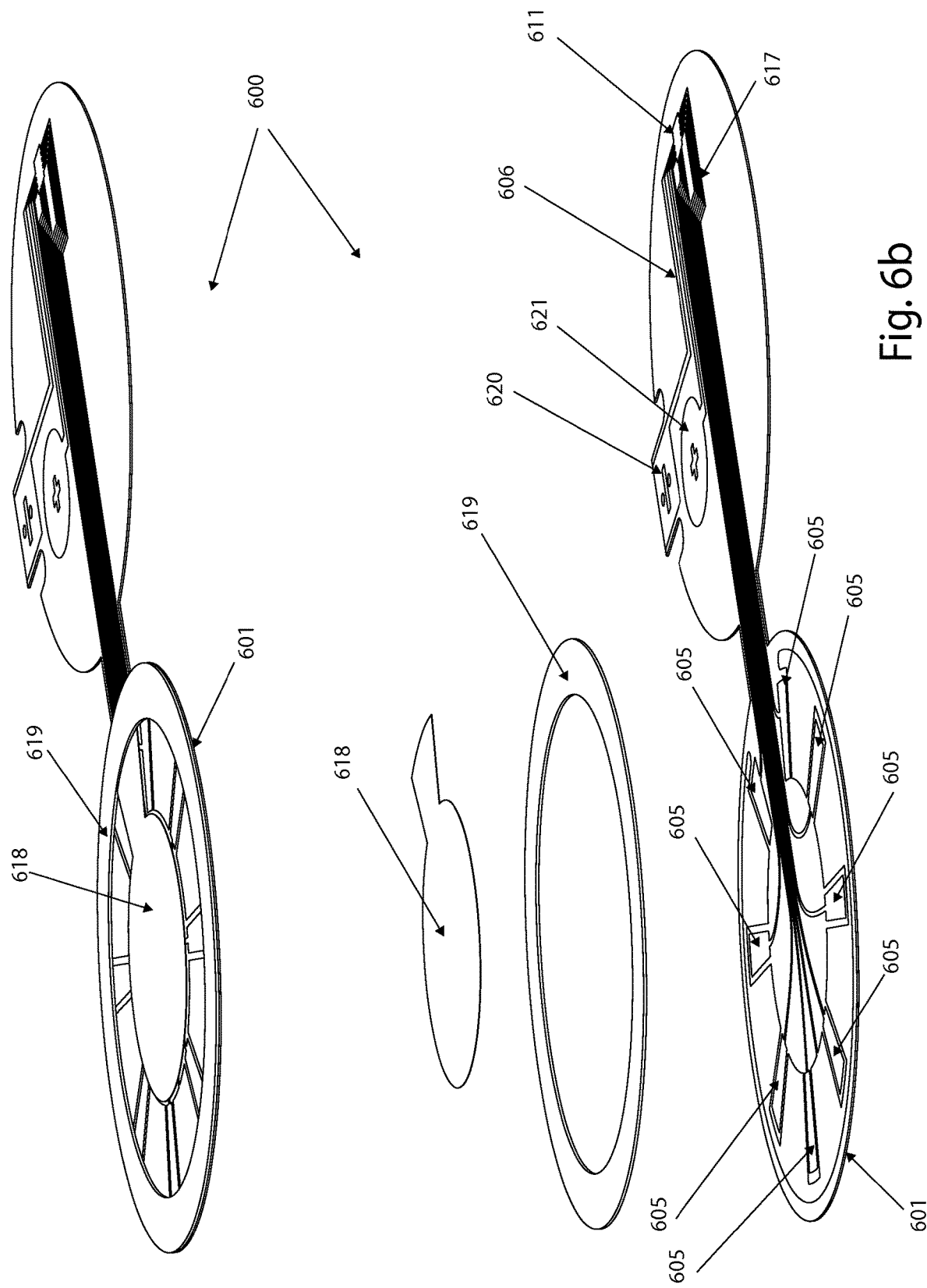
Figure 6C:
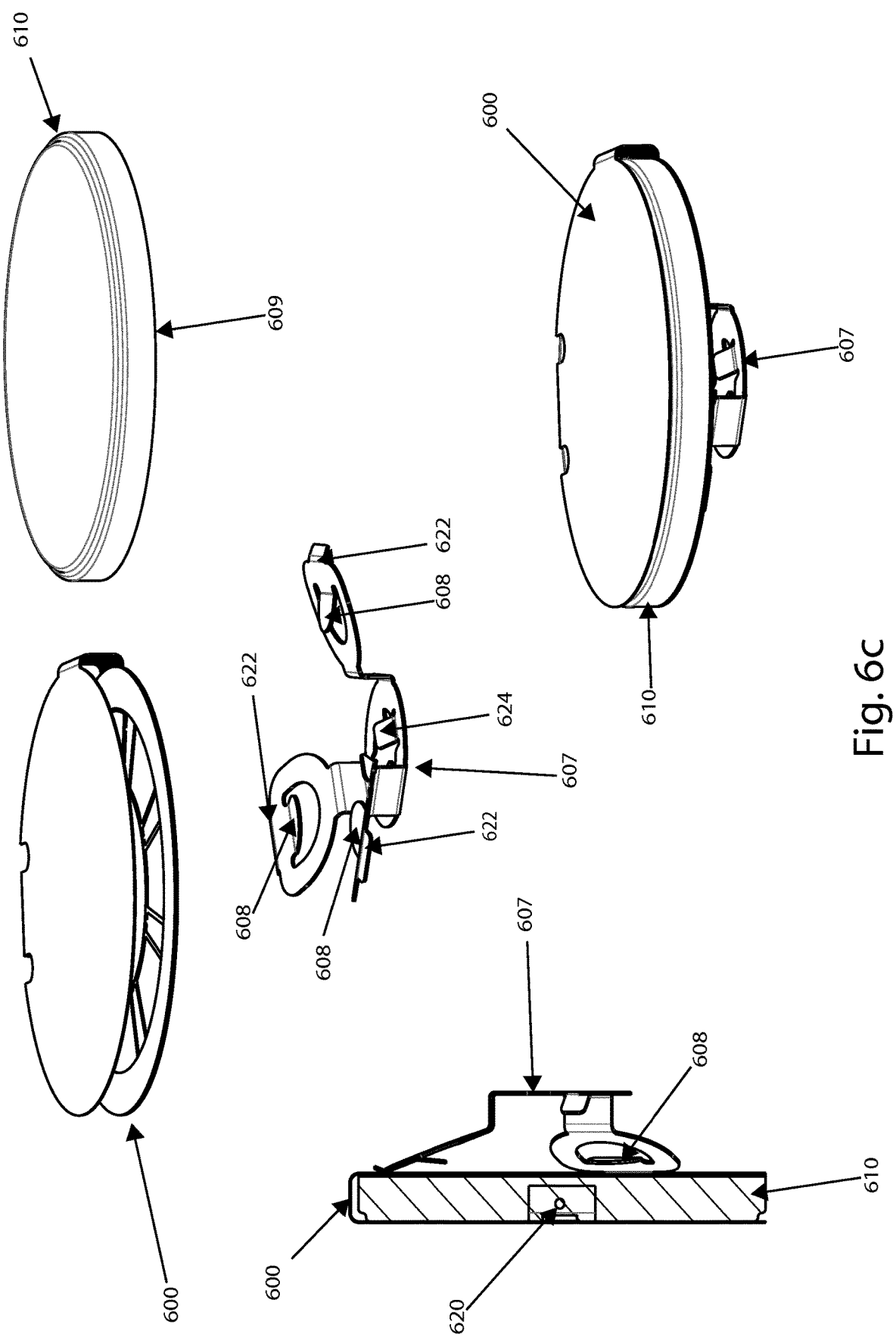

In FIGS. 6*a*-*c* is shown another embodiment of a module. FIG. 6*a* shows a flexible printed circuit board sheet 600 comprising individual conductive sensor areas 605 separated by areas 625, electrical conductors 606 and processor unit 611. Each of the sensor areas 605 is connected to the processor unit 611, whereas the areas 625 are not connected to a conductor and are thus not part of the electrical circuit. A communication unit 617 is disposed on the flexible printed circuit board sheet and adapted to wirelessly communicate data to an external device.

Spacers 618, 619 are arranged to provide axial spacing between the conductive sensor areas 605 and a second surface area, in this embodiment a surface 609 of the battery 610, see FIG. 6c. The spacers 618, 619 provide axial spacing to avoid unwanted connections to occur while still enabling the individual sensor areas 605 to be brought into galvanic conductive contact with the surface area 609 of the battery 610 when acted upon by the second sensor part 607. The second sensor part 607 has three flexible arms ("wipers") each with a structure 608 adapted to deflect different sensor areas 605 into contact with the surface 609 of the battery (the (−) terminal) when the structure 608 overlaps a sensor area 605.

When the sensor unit is an inactive state, only the support surfaces 622 of the arms will engage the flexible printed circuit board sheet on the side opposite to side facing surface areas 609 of the battery, as shown in the leftmost drawing of FIG. 6c. When an axial force is applied to the second sensor part in a direction towards the first sensor part, or vice versa, i.e. the module is being compressed, the arms will deflect outwards and thereby forcing the structures 608 into engagement with the areas 605 and 625, respectively.

The second sensor part 607 has attachment means 624 allowing the second sensor part to be attached, either directly or indirectly, to the piston rod such that no relative rotation between the second sensor part and the piston rod is possible.

+ and − terminals 620, 621 are provided on the flexible printed circuit board sheet for connection to the terminals of the battery 610.

Figure 7:
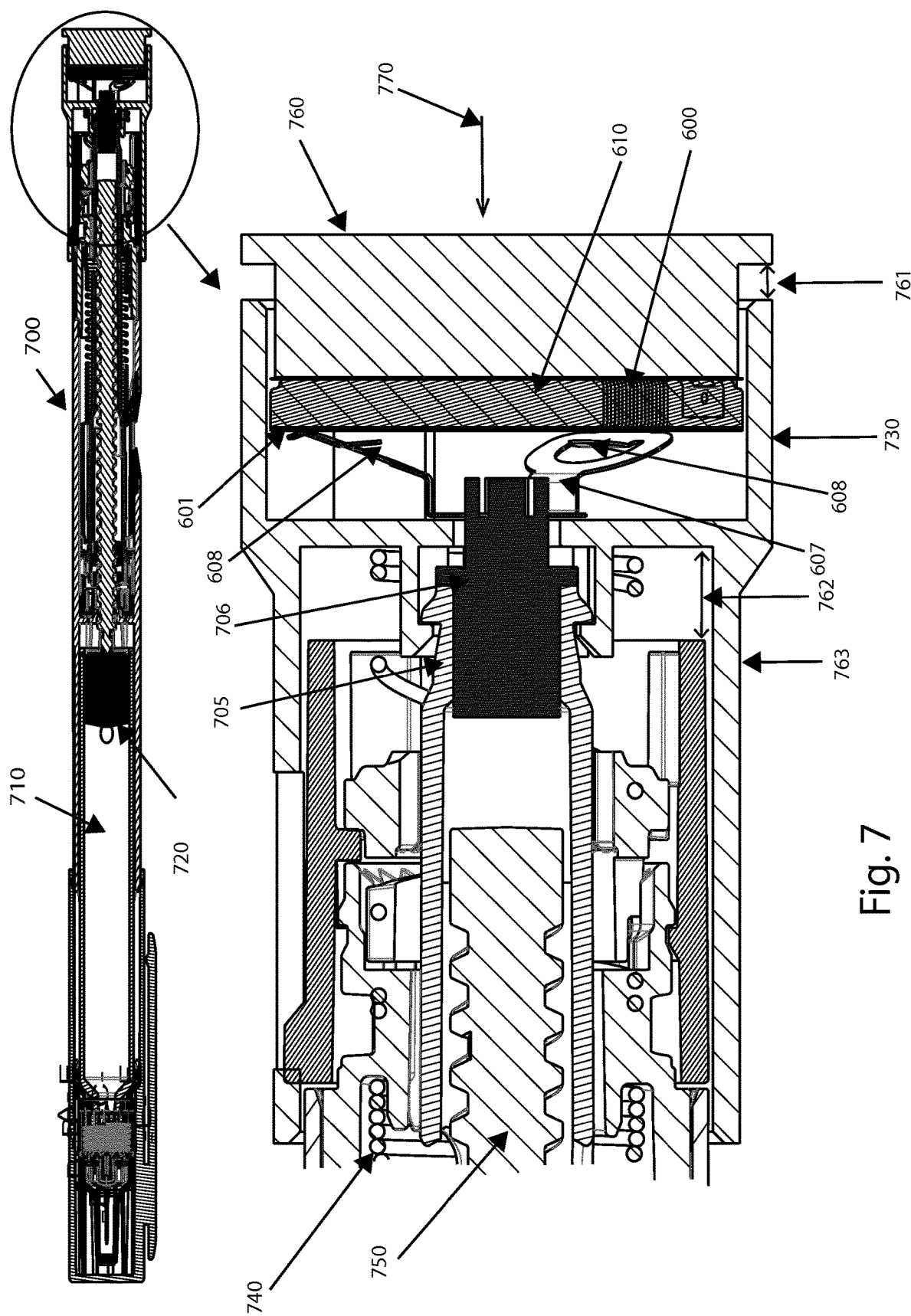
FIG. 7 shows a cross sectional view of the module as shown in FIGS. 6a-c arranged inside a pen drug delivery device.

FIG. 7 shows a cross sectional view of a module as shown in FIGS. 6a-c arranged inside a pen drug delivery device 700. Compared to the embodiment shown in FIGS. 2 and 3a-c, the module in FIG. 7 is positioned in a proximal end of the pen opposite to the end in which the drug-filled cartridge 710. The pen has a dose ring member 730 serving to manually set a desired dose of drug. The pen has a spring 740 which is strained during dose setting and then released to drive the piston rod 750 rotationally and axially towards the distal end of the pen to advance the piston 720 and thereby expel a dose, when the release button 760 is actuated in an axial direction 770.

The module is positioned such that the second sensor part 607 of the sensor unit is engaged and rotationally locked to a drive tube 705 via the element 706, the drive tube being in engagement with the piston rod 750 to rotationally drive the piston rod during dose expelling, meaning that the second sensor part 607 is indirectly fixed to the piston rod and will follow the rotation thereof during dose expelling. The first sensor part 601 of the sensor unit is arranged axially offset to the second sensor part 607 and perpendicularly relative to the axis of rotation and is fixed in the pen such that it doesn't rotate during dose expelling.

The flexible printed circuit board sheet 600 is folded around the battery 610.

The pen with the module as shown in FIG. 7 functions as follows; the desired dose of drug to be expelled is set by rotating the dose ring member 730 until the desired dose is shown in a window on the pen. During dose setting the spring 740 is strained to build up a driving force needed to drive the piston rod 750 forward during dose expelling. During the dose setting there is no electrical connection to the conductive sensor areas and the sensor unit is inactive ("dose setting mode").

To expel the set dose, the injection button 760 is pushed axially in the direction 770, whereby the first sensor part 601 together with battery etc. is moved axially towards the second sensor part 607. When the injection button is moved the distance 761, the spring hasn't been released yet, but the structure 608 have deflected a respective conductive sensor area 605 into connection with the surface 606 to connect it to the electrical circuit and the sensor unit is then activated ("dose expelling mode") and the processor unit will get signals indicative of the start position of the sensor unit. When the injection button is pushed further axially, both the injection button 760 and the part 763 will move together the distance 762 and the spring 740 will be released. Now the drive tube 706 and accordingly the piston rod 750 will start rotating and advance axially toward the piston 720 to expel the dose. As the second sensor part 607 is rotationally locked to the piston rod via the drive tube, it will start rotating together with piston rod and the structures 608 will then in turn deflect respective conductive sensor areas 605 into connection with the surface 609 of the battery. The established connections generate an electrical signal, as explained above, to the processor unit, said signal being indicative of the relative rotational position between the first and second sensor part.

Figure 8:
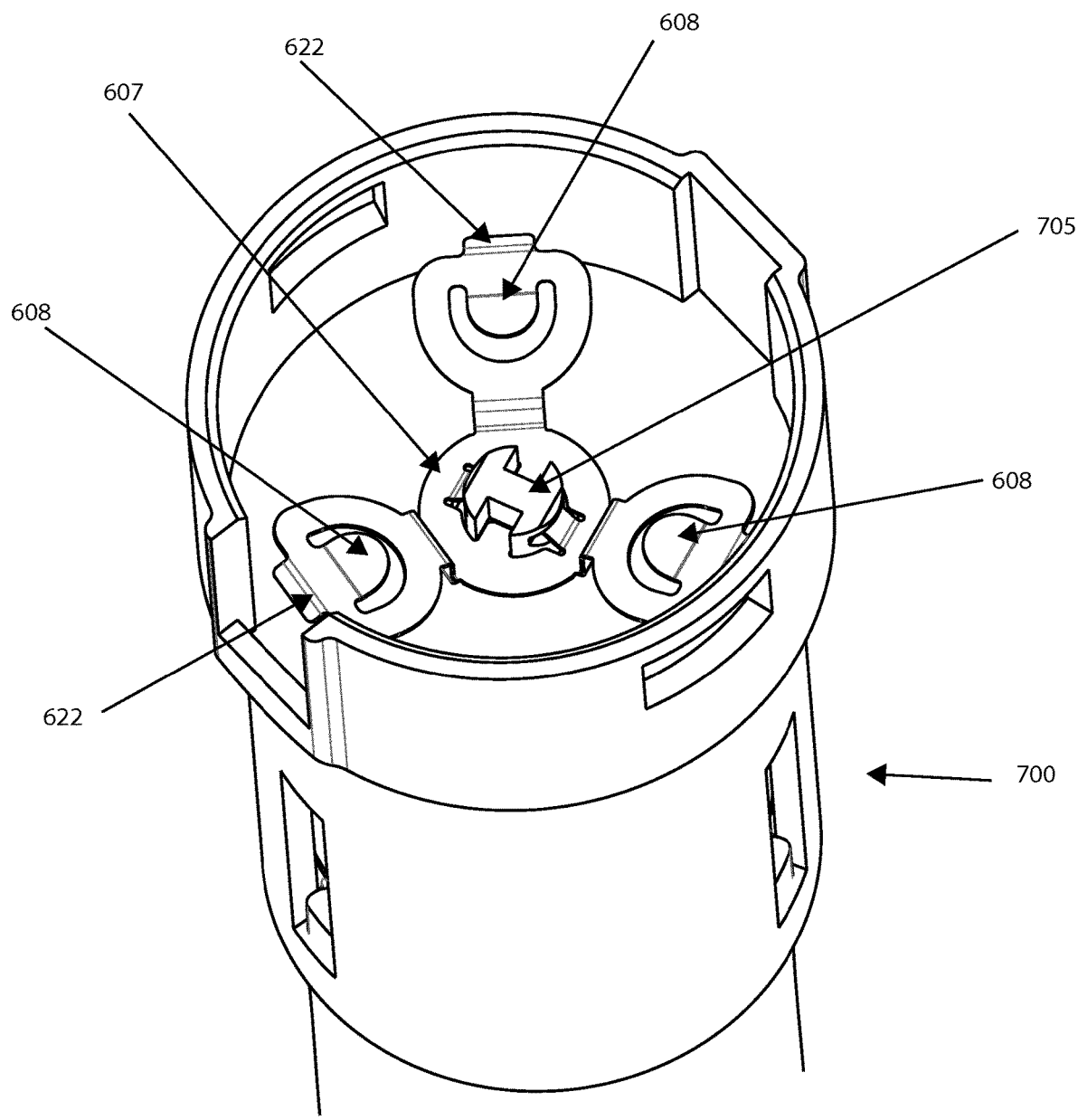
FIG. 8 shows the second sensor part of the module shown in FIG. 7 arranged inside a pen drug delivery device.

FIG. 8 shows the second sensor part 607 of the module arranged inside the pen drug delivery device 700. The second sensor part 607 with the structure 608 and support surfaces 622 is fixedly attached to the piston rod via the drive tube 705, so that it follows the rotation of the drive tube 705 and thereby the piston rod during dose expelling.

FIGS. 9a-h show the connection sequences of the sensor unit of FIG. 6c, when the first and second sensor parts rotate relative to each other during dose expelling.

In FIG. 9a the sensor unit is in its initial start position, where no drug has been expelled yet but the one structure 608 of second sensor part has closed the electrical circuit between the (−) terminal and the processor unit for conductive sensor area 605 by deflecting it into conductive electrical connection with the conductive surface area 609 ((−) terminal) of the battery. The sensor unit is now turned "on" and ready to sense relative rotations. None of the other conductive sensor areas of the first sensor part are in conductive connection with the surface of the battery at this stage.

In FIG. 9b the second sensor part has been rotated 15 degrees clockwise compared to the positon in FIG. 9a, so that another structure 608 has provided conductive connection between another conductive sensor area 605 and the surface area 609. In FIG. 9c the second sensor part has been rotated 15 degrees clockwise compared to the position in FIG. 9b and so forth.

Figure 10D:
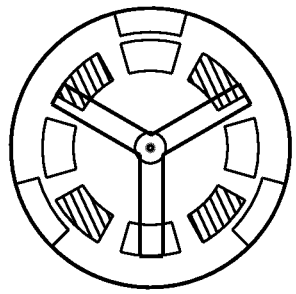
Figure 10H:
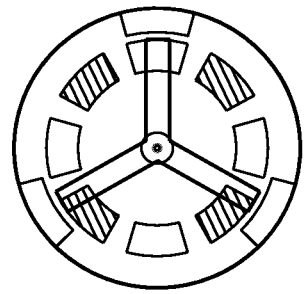
Figure 10C:
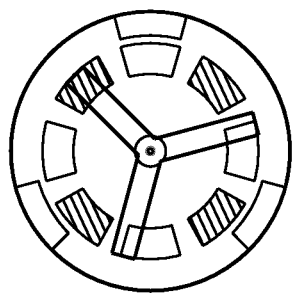
Figure 10G:
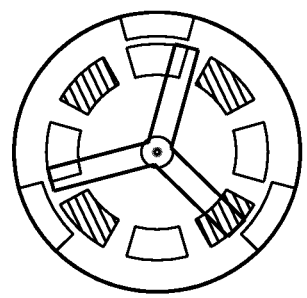
Figure 10B:
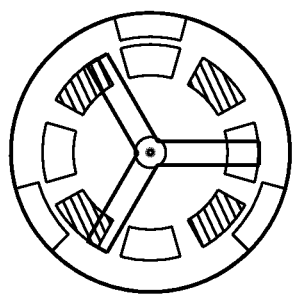
Figure 10F:
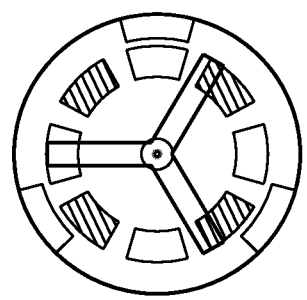
Figure 10A:
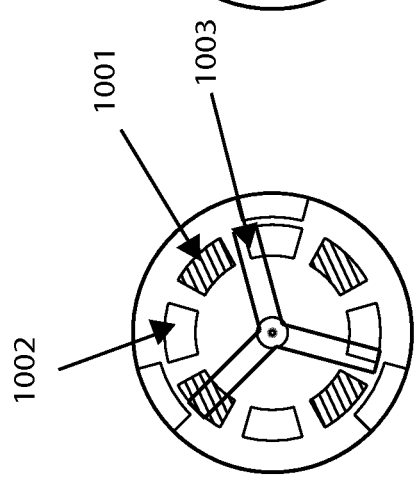
Figure 10E:
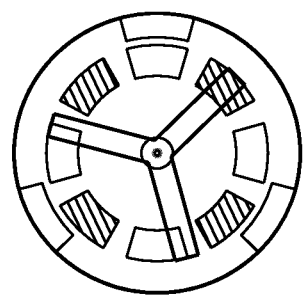

FIGS. 10a-h show an example of connection sequences of a module according to the invention. The first sensor part has four conductive sensor areas 1001 (shaded) in the form of arc-segments evenly distributed around a circle, i.e. 90 degrees between, each connected to a processor unit. The four other conductive sensor areas 1002 (non shaded) are connected to the (−) terminal of a power source unit. The second sensor part has three arms 1003 positioned with 120 degrees between each. In FIG. 10a the sensor unit is in its initial start position, where no drug has been expelled. In FIG. 10b the second sensor part has been rotated 15 degrees counter clockwise compared to the positon in FIG. 10a, so that another structure of second sensor part has closed the electrical circuit between (−) terminal and the processor unit (not shown) for a further conductive sensor area. In FIG. 10*c* the second sensor part has been rotated 15 degrees counter clockwise compared to the position in FIG. 10*b* and so forth.

The code pattern for the embodiments of the module shown in the figures is based on a "resolution" of 15 degrees of rotations between each connection, which for a given drug formulation and delivery device combination may correspond to 1 unit (IU) of insulin, i.e. one full 360 degrees revolution of the piston rod corresponds to 24 units (IU). As can be seen in the FIGS. 9*a-h* and 10*a-h*, the sensor configuration with three arms (wipers) and four or eight conductive sensor areas creates a pattern that repeats after eight rotations of 15 degrees, equal to eight units of insulin. In a spring driven pen device, where the spring force typically will force the piston rod to rotate very fast during injection of the first 2-6 units, the sensor unit may jump some connections. However, by using the sensor configurations shown there are only eight units of absolute placement of the sensor, why the determination of the relative position between the first and second sensor part of the sensor still is reliable, even if the sensor may jump some connections.

Further, the use of only three arms has the advantage that the friction force between the first and second sensor part is kept low (the fewer arms the lower friction) and that the torque is the same on all three arms, as long as the arms are made of flexible material.

For a drug formulation having the double concentration a 7.5 degree rotary "resolution" would be necessary to register dose steps corresponding to 1 IU of insulin, unless each dose step equals 2 IU and instead of 1 IU.

As a given dose of drug, especially if large, may be divided and injected with a given pause, the module may be programmed to log two dose amounts expelled within a given time window, e.g. 15 minutes, as one dose.

Figure 11:
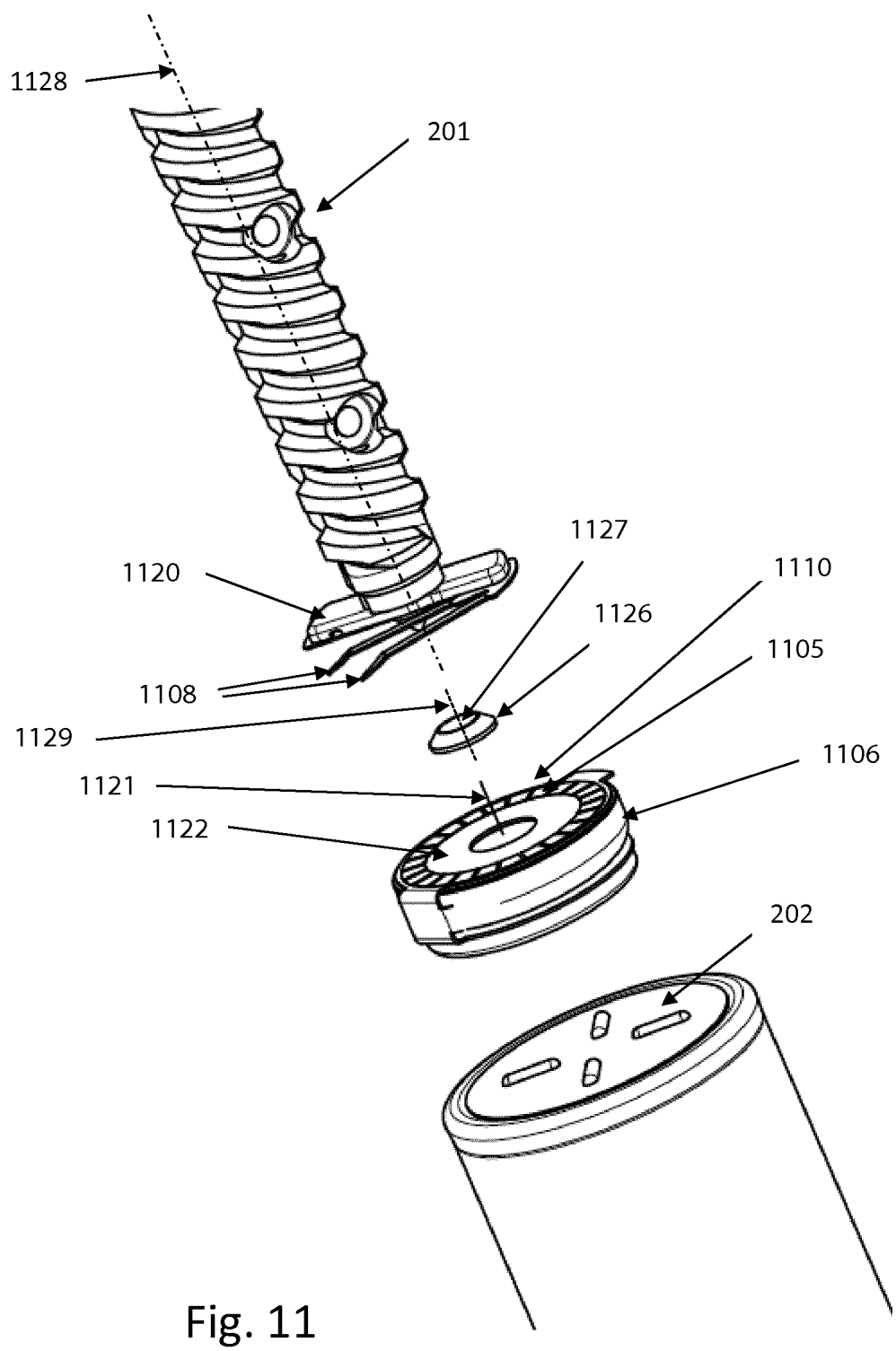
FIG. 11 shows an exploded view of a further rotary sensor module according to the invention.

An exploded view of a rotary sensor module according to the invention is shown in FIG. 11. A rotary sensor module comprises a first sensor part 1110 in the form of a flexible printed circuit board sheet having a surface 1122 with twentyfour individual electrically conductive sensor areas 1105 distributed circumferentially around a centre axis B, 1121, of the first sensor part and some of which are connected to (−) terminal and some of which being connected to processor unit. The first sensor part is adapted to engage directly or indirectly the piston 202 of the drug-filled cartridge and thereby provides an engagement between the first sensor part 1105 and the piston 202, such that no relative rotation there between is possible.

The rotary sensor module further comprises a second sensor part 1120 oppositely arranged to said surface 1122 of the first sensor part 1110 and mounted to the piston rod 201 at its distal tip part 1125 to follow the rotation of the piston rod during dose expelling. The piston rod has a centre axis A, 1128, around which is rotates during dose expelling.

The second sensor part has contact structures 1108 in the form of two electrically connected flexible arms that are connected to the (−) terminal of the battery and adapted to engage and electrically connect different individual electrically conductive sensor areas 1105 of the first sensor part, upon relative rotational movement between the first and second sensor part, to the processor unit to thereby close an electrical circuit between the (−) and the processor unit. Each of these electrical connections generates an electrical signal to a processor unit being indicative of the rotational position between the first and second sensor part. See more detailed description of this in connection with FIGS. 13*a-b*.

A centering element 1126 is provided between the first and second sensor part for centering the piston rod and thereby the second sensor part 1120 in relation to the first sensor part 1110, which is essential for the rotary sensor to measure the correct amount of relative rotations between the piston rod and piston. The centering element 1126 comprises a bearing cup part 1127 with a centre axis C, 1129, for maintaining the distal part of piston rod, in this situation a part of the second sensor part 1120, in a position where the axis' 1121, 1128 are coinciding.

To provide a proper centering, the bearing cup part 1127 can have different forms as depicted in FIGS. 14*a-d*.

Figure 12A:
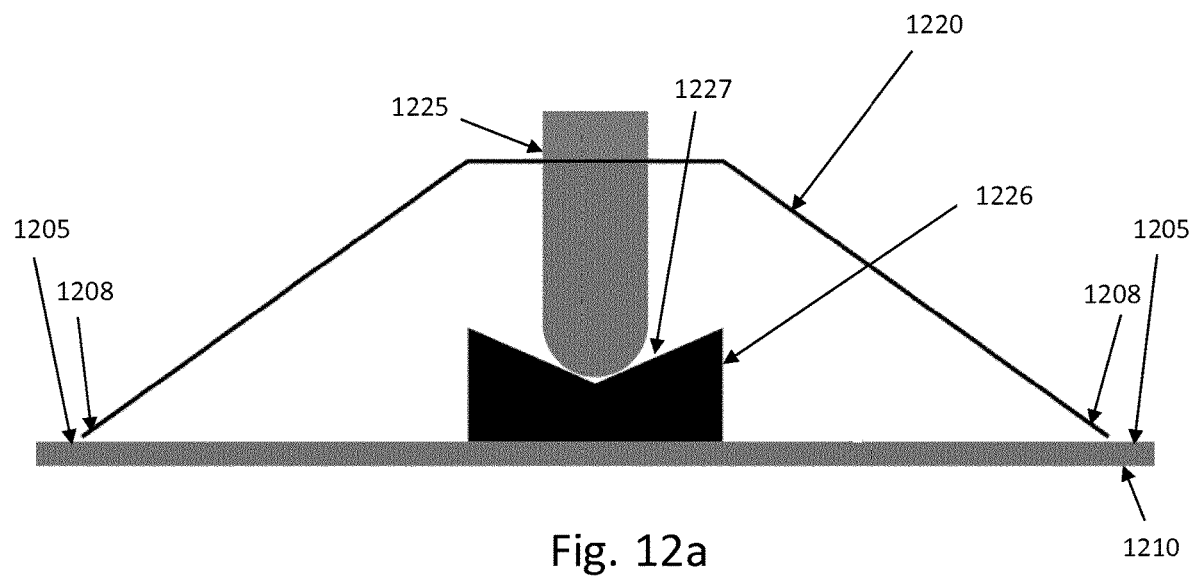
FIGS. 12a-b show cross sectional views of exemplary embodiments of a rotary sensor module according to the invention.

In FIG. 12*a* is shown a cross sectional view of an exemplary embodiment of a rotary sensor module, where the second sensor part 1220 is attached to the distal part 1225 of the piston rod to follow the rotation of the piston rod. The centering element 1226 is attached to the first sensor part 1210, such that the center axis of the bearing cup part is coinciding with the center axis of the first sensor part. The distal tip part is centered via the bearing cup part, whereby a complete alignment between the first sensor part and the piston rod and thereby second sensor part is achieved. The alignment ensures that the contact structures 1208 always maintain contact with the surface 1222 and thereby generate a proper signal for each and every single mutual relative rotary movement between the sensor parts. Without the centering element, the two sensor parts may wobble in relation to each other as the piston rod rotates, whereby the structures of the second sensor part may jump over some of the conductive sensor areas of the first sensor part and generate a fault or no signal.

During dose expelling the piston rod is rotated and advanced axially in the direction of the piston in order to advance the piston forward in the cartridge. Thus, the piston rod will exert an axial force on the piston via the rotary sensor module and due to the centering element the torque required to rotate the piston rod in relation to the piston is minimised, as the centering element ensures that the mechanical contact between the parts rotating relative to each other is kept at the axis of rotation. The torque required can be even more minimised depending on the design of the centering element, see FIGS. 14*a-d*.

The centering element may be fixedly attached to the first sensor part by different appropriate means, such as by riveting, soldering or gluing. If soldered, the centering element can function as an electrical contact between e.g. the (−) terminal and the second sensor part, as shown and described in FIG. 12*b*.

Figure 12B:
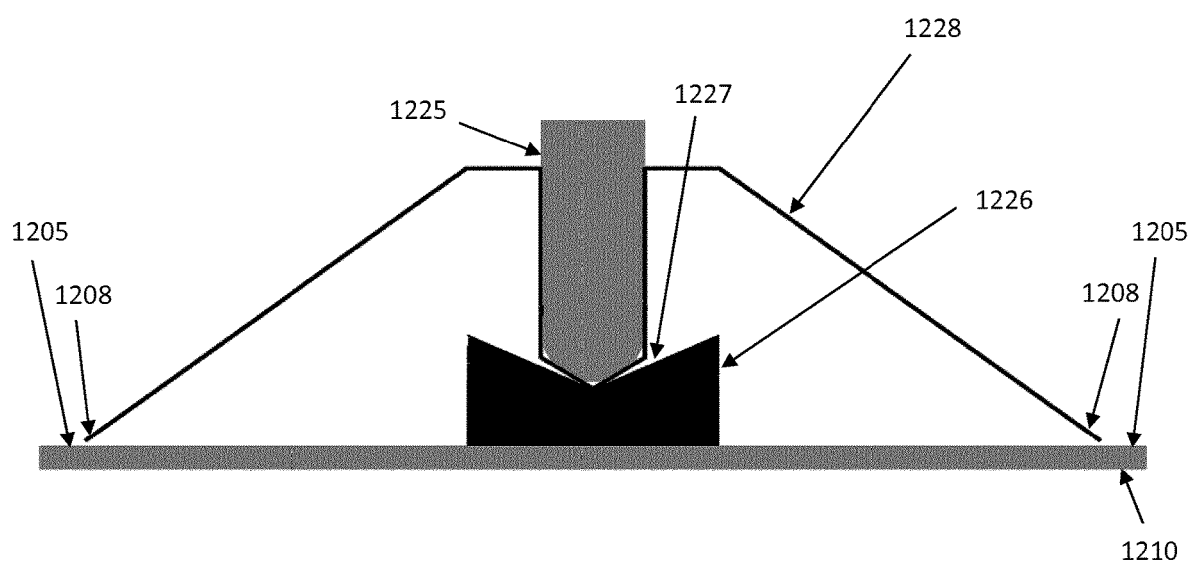

In FIG. 12*b* is shown cross sectional view of another exemplary embodiment of a rotary sensor module, where the second sensor part 1220 is attached to the distal part 1225 of the piston rod to follow the rotation of the piston rod. In this embodiment, the centering element 1226 and the bearing cup part 1227 is made of electrically conductive material and is electrically connected to the (−) terminal of the battery (not shown in the figure). The second sensor part is electrically connected to the bearing cup part as shown, which allows for an electrical ground signal to be passed via the centering element to the second sensor part.

Figure 13A:
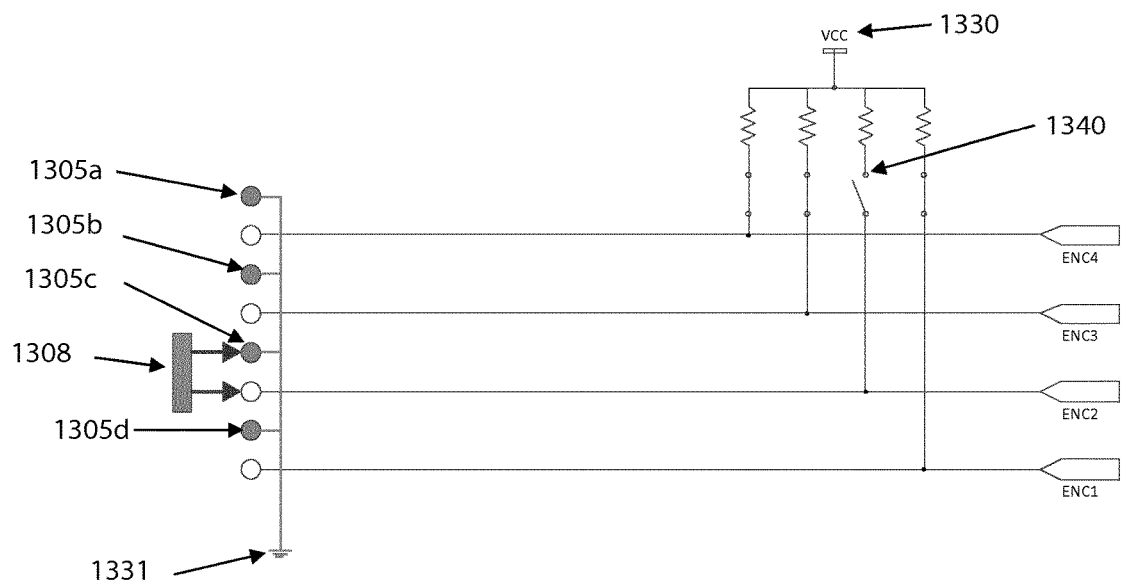
FIGS. 13a-b show examples of the electrical circuit for the rotary sensor module according to the invention.
Figure 13B:
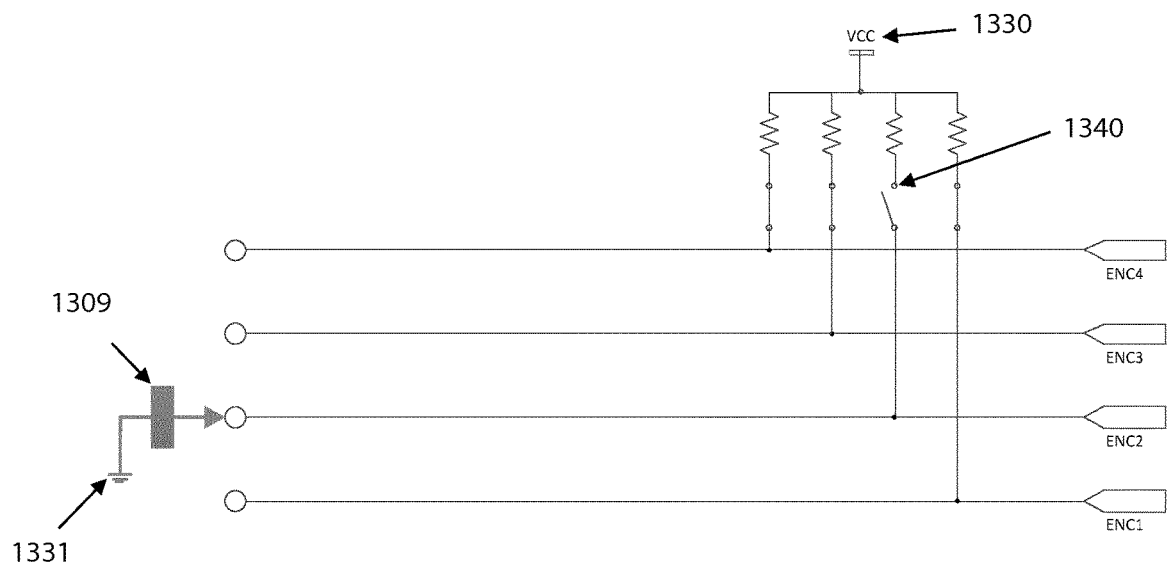

In FIGS. 13*a-b*, the conductive sensor areas (ENC1, ENC2, ENC3, ENC4) of the first sensor part are connected to the power source 1330 ("VCC", (+) terminal) via the processor unit and the conductive sensor areas (1305*a*, 1305*b*, 1305*c*, 1305*d*) are connected to the (−) terminal 1331 (ground). The contact structure 1308 of the second sensor part will, as the first and second sensor parts rotate relative to each other, connect the different conductive sensor areas (ENC1, ENC2, ENC3, ENC4) and close the electrical circuit between the (−) terminal and the processor unit. As a sensor area (ENC1, ENC2, ENC3, ENC4) is connected to ground the electrical circuit is closed and the specific sensor area is turned "on" and a signal will be generated to the processor unit. The readout for the specific sensor area that is turned on will be a "1" and the readout for a sensor area that is turned off will be "0". In the example shown in FIG. 13a, the "ENC2" is connected, as the contact structure 1308 close the electrical circuit to (−) terminal and processor unit, why the readout in the processor unit for this specific relative position between the first and second sensor part will be "0", "1", "0", "0" for the sensor areas ENC1, ENC2, ENC3 and ENC4, respectively. Based on the readouts the processor unit can determine the amount of relative rotations between the sensor parts and thereby between the piston rod and piston of the injection device. Knowing the amount of relative rotations between the piston rod and piston, the size of the dose expelled from the injection device can be determined and stored in the processor unit.

In order to save power, the processor unit may, immediately after registering the readout of a sensor area (ENC1, ENC2, ENC3, ENC4), switch the electrical circuit "off" for that specific sensor area. This is shown in the diagram in FIG. 13a, where the electrical switch mechanism 1340 is "open" for ENC2. The electrical switch mechanism may be in the form of a pull-up resistor to open the electrical circuit to a sensor area after the electrical circuit has been closed and an electrical signal has been received by the processor unit for the sensor area, the pull-up resistor being controlled by the processor unit. This will effectively save power as the sensor areas don't need to be powered up all the time to monitor sensor transitions. However, a detection of the next transition for this specific sensor area will not be detected as the electrical circuit is open by the pull-up resistor. A way of reducing this problem is to implement an intelligent control of the pull-up resistors. Initially, only pull-up resistors for all open electrical circuits are activated. When a sensor transition is detected all pull-up resistors are activated, allowing software in the processor unit to detect all sensor transitions and a timer is started. Every time a sensor transition is detected, the timer is reset to its original value, and when the timer times out, the system reverts to only having the pull-up resistors for open electrical circuits activated. The sensor will consume power during and shortly after a detected transition but will zero-power when static.

FIG. 13b shows the electronic circuit of the embodiment of the sensor module shown in FIG. 3b. In this more simple embodiment, the ground (−) terminal 1331 is connected to the second sensor part only, i.e. none of the conductive sensor areas of the first sensor part is connected to ground. The ground (−) connection to the second sensor part may e.g. be via the centering element, as shown and described under FIG. 13b above.

FIG. 14a-d shows various cross-sectional views of the bearing cup part of the centering element according to the invention. The choice of cross-sectional view is a compromise between level of mechanical play between the centered parts in the bearing cup part and the friction force and thereby torque added by the centering element to rotate the piston rod relative to the piston. It is preferred to have best possible centering while adding minimum of friction and torque, the latter to obtain as low injection force needed to expel a dose of drug.

Figure 14A:
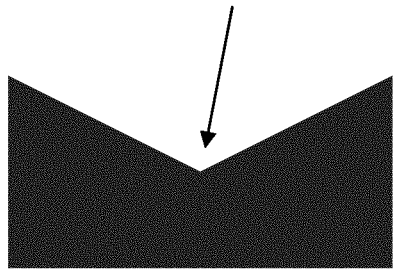
FIG. 14a-d show different embodiments of the centering element with different cross-sections.

FIG. 14a shows a V-shaped cross-section 1427a, which ensures proper centering with little to no mechanical play in the bearing.

Figure 14B:
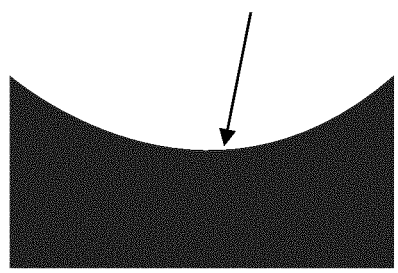

FIG. 14b shows a U-shaped cross-section 1427b, which ensures proper centering with very little mechanical play and only a single point of contact reducing friction between the piston rod and centering element.

Figure 14C:
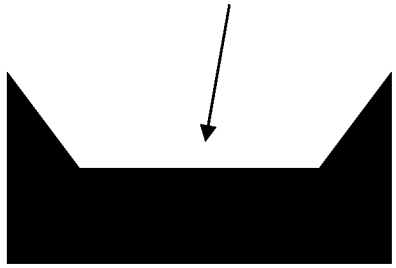

FIG. 14c shows a trapezoid shape 1427c, which improves centering but do allow for some mechanical play.

Figure 14D:
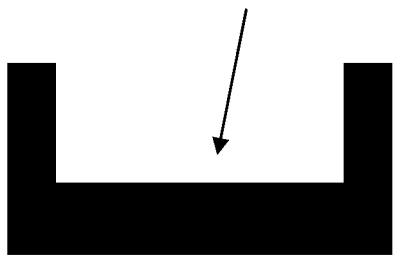

FIG. 14d shows a square shape 1427d, which improves centering but do allow for some mechanical play.

Figure 15:
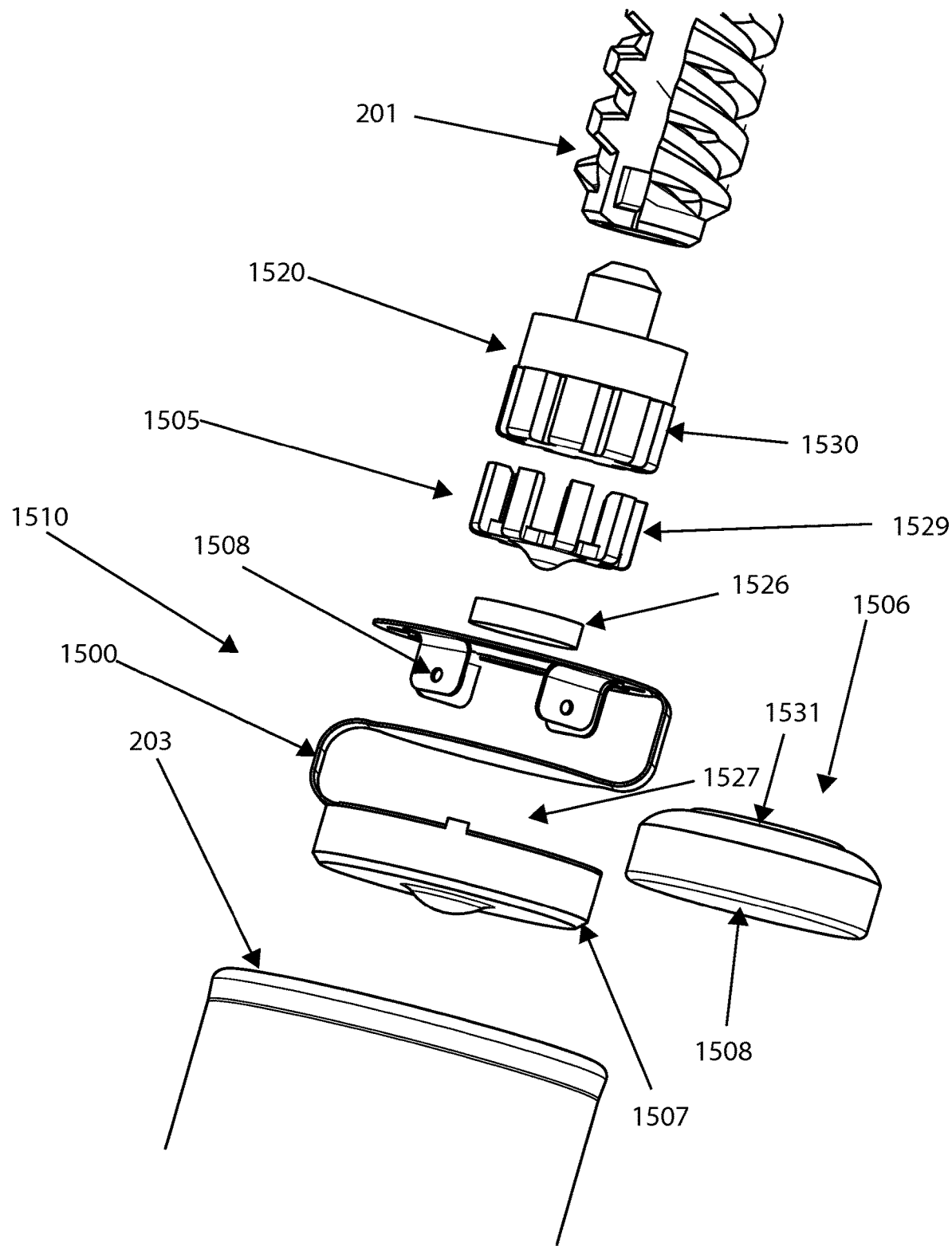
FIG. 15 shows an exploded view of another embodiment of a rotary sensor module according to the invention.

FIG. 15 shows an exploded view of an alternative embodiment of a rotary sensor module according to the invention. A first cylindrical formed rotary sensor part 1520 to be connected to the piston rod comprises a plurality of individual electrically conductive sensor areas 1505 (in this example nine sensor areas) arranged in a pattern spaced apart around a cylindrical surface on the part 1529 and extending parallel to the axis of rotation of the piston rod. The rotary sensor part 1520 consists of two components, a metal part 1529 with the conductive sensor areas 1505 and non-conductive plastic part 1530. In an assembled version, the metal part 1529 may be over moulded with the non-conductive plastic part.

The module further comprises a second stationary sensor part 1510 comprising a flexible printed circuit board sheet 1500 on which are located contact structures 1508 extending parallel to the axis of rotation of the piston rod. The flexible sheet 1500 is folded around a cell coin battery 1506 (see FIG. 16) and the contact structures are connected to the (+) terminal 1528 via the processor unit 1507. The second sensor part is adapted to be fixed to the piston in the cartridge 203 in a manner that allow no rotation between the piston and the sensor part.

A centering element 1526 is located between the two sensor parts and is made of conductive material. When assembled (see FIG. 16) the centering element engages the (−) terminal 1531 of the battery either directly or through the flexible sheet 1500 having conductive material located between the centering element and the (−) terminal 1531. Thereby, the sensor areas 1505 are connected to the (−) terminal 1531. The centering element further centers the piston rod 201 and thereby the sensor part 1520 in relation to the sensor part 1510 to ensure a proper alignment between the sensor parts and thereby an accurate readout from the sensor module.

The module preferably also comprise a communication unit to wirelessly communicate data (dose size, timestamp) from the module to an external device.

Figure 16:
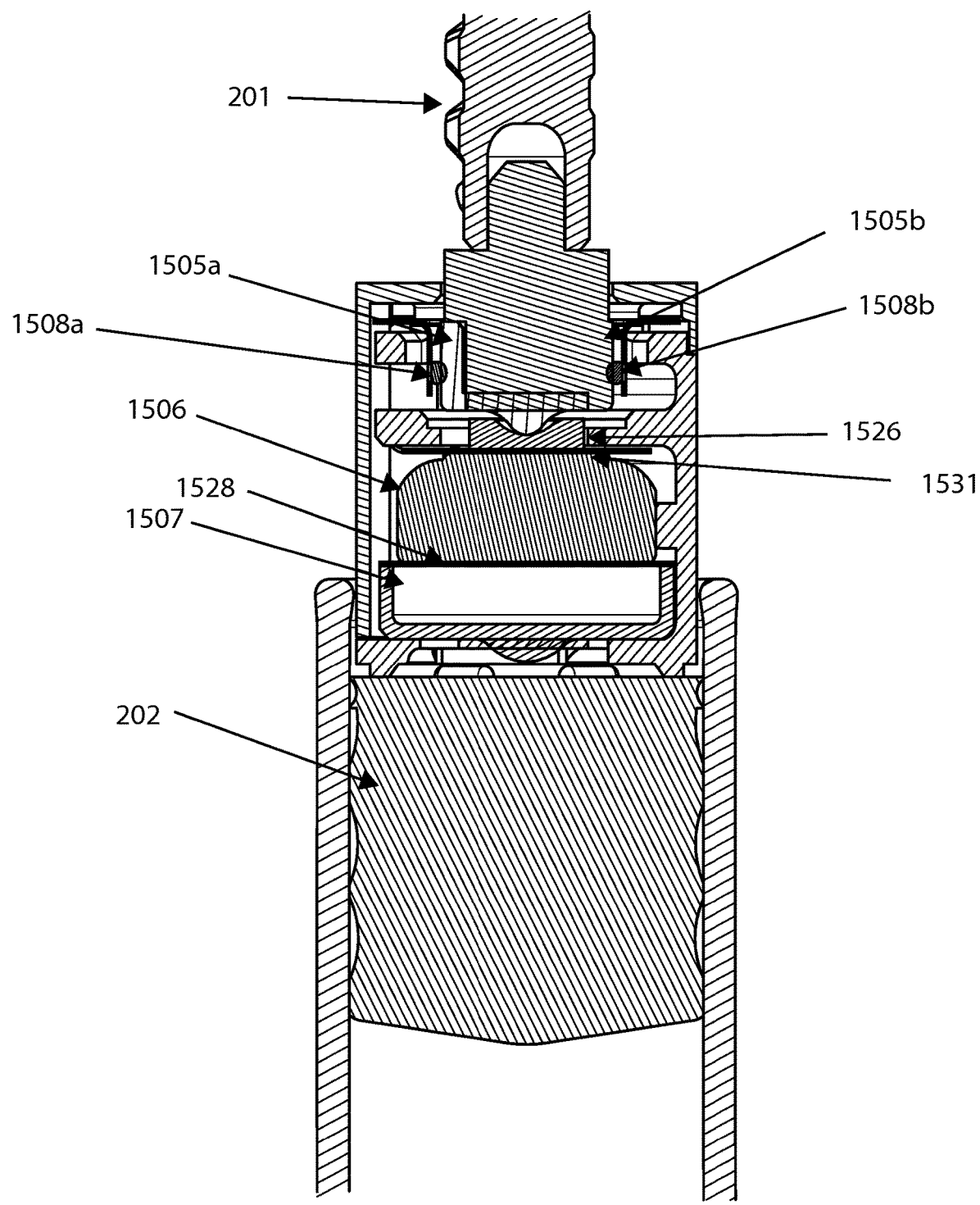
FIG. 16 shows a cross-sectional view of the sensor module shown in FIG. 15.

FIG. 16 shows a cross-sectional view of the sensor module of FIG. 15 positioned in the pen drug delivery device, where the first rotary sensor part is co-axially and partly located inside the second stationary sensor part.

As the piston rod rotates during dose expelling, the contact structures 1508 (four in total) will electrically connect to different individual electrically conductive sensor areas 1505. In FIG. 16 it can be seen that contact structure (or switch) 1508a (a round metallic ball) is electrically in contact with a sensor area 1505a, whereby electricity is conducted from (−) terminal 1531 via the conductive centering element 1526 all the way to the contact structure 1508a and to the processor unit 1507, i.e. the electrical circuit is closed and the processor receives an electrical signal indicating e.g. an "on" or "1" for this specific sensor area 1505a. Whereas to the right side, the contact structure 1508b is in contact with a non-conductive area, i.e. it is open and the processor unit will recognise it as "off" or "0". Each time a contact structure connects to a sensor area an electrical circuit will be closed and the processor unit receive an electrical signal, each electrical being indicative of the rotational position between the first and second sensor part. It means that during an injection of drug, electrical circuits will be closed or open depending on the mutual position between the first and second sensor part and generate electrical signals to the processor unit. Each of these positions will be translated into the amount of relative rotations between the first and second sensor part and thereby no. of rotations of the piston rod. Based on the no. of rotations of the piston rod, the expelled dose of drug can be determined by the processor unit. This information together with a timestamp for when the injection was taken can be transferred wirelessly to a receiving unit. e.g. a mobile phone.

For any of the described embodiments above the conductive sensor areas and the contact structures together are configured to create a code pattern of contact positions (encoder) indicative of the rotational positions between the first and second sensor part. The indexing code pattern may be based on a Gray code system or quadrature code system or any other relevant system. The Gray code could e.g. be a 4 bit 72 increment encoder system, where the pattern repeats 9 times for each 360 degrees revolution.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A rotary dosage sensing module for a pen drug delivery device comprising a drug-filled cartridge with a displaceable piston and an outlet and a piston rod to be axially advanced in a direction towards said piston to displace the piston and thereby expel a dosage of drug from the cartridge through the outlet, the piston rod rotating relative to the piston around an axis of rotation (A) during axial movement, said module comprising:
a power source unit with a (−) and a (+) terminal,
a processor unit connected to the (−) and (+) terminals of the power source unit,
a sensor unit comprising;
a first sensor part adapted to be directly or indirectly fixed to a part of the pen drug delivery device not rotating during dose expelling, the first sensor part comprising a flexible printed circuit board sheet having a first surface on which is disposed a plurality of individual electrical conductive sensor areas arranged in a pattern, some of which being electrically connected to the (−) terminal of the power source unit and some of which being connected to the processor unit, wherein the flexible printed circuit board sheet is folded around and adhered to the power source unit and where said first surface is supported by a surface of the power source unit,
a second sensor part arranged opposite to the first sensor part and adapted to be directly or indirectly fixed to the piston rod to follow the rotation of the piston rod during dose expelling, the second sensor part comprising a plurality of electrically connected contact structures, and wherein the plurality of electrically connected contact structures are connected to the (−) terminal of the power source unit via those electrically conductive sensor areas that are connected to the (−) terminal of the power source unit, the plurality of electrically connected contact structures being adapted to, upon relative rotational movement between the first and second sensor part, electrically connect different individual electrically conductive sensor areas to the processor unit to thereby close an electrical circuit between the (−) terminal and the processor unit for the different conductive sensor area, each electrical connection generating an electrical signal to the processor unit being indicative of the rotational position between the first and second sensor part, and wherein the processor unit is adapted to process said electrical signals to determine the amount of relative rotations between the first and second sensor part and thereby calculate the expelled dosage size based on the determined amount of relative rotations.

2. The module according to claim 1, further comprising an electrical switch mechanism to open the electrical circuit to a sensor area of the plurality of individual electrical conductive sensor areas after the electrical circuit has been closed and an electrical signal has been received by the processor unit for the sensor area, the switch mechanism being controlled by the processor unit.

3. The module according to claim 2, wherein the electrical switch mechanism comprises a pull-up resistor to open the electrical circuit to a sensor area of the plurality of individual electrical conductive sensor areas a predefined time after the electrical circuit has been closed and an electrical signal has been received by the processor unit for the sensor area, the pull-up resistor being controlled by the processor unit.

4. The module according to claim 1, wherein the plurality of individual electrical conductive sensor areas are distributed circumferentially around a centre axis (B) on said first surface of the first sensor part, and wherein the module further comprises a centering element with a bearing cup part having a centre axis (C) and arranged in relation to the first sensor part such that said centre axis (C) coincides with the centre axis (B), the bearing cup part being adapted to maintain a distal tip part of the piston rod in a position, during dose expelling, where the axis of rotation (A) is coinciding with the centre axis (B).

5. The module according to claim 4, wherein the second sensor part is adapted to form part of the distal tip part of the piston rod, and wherein the bearing cup part is adapted to receive and maintain the part of the second sensor part forming the distal tip part in a position, during dose expelling, where the axis of rotation (A) is coinciding with the centre axis (B).

6. The module according to claim 4, wherein the bearing cup part is made of electrically conductive material and electrically connected to the (−) terminal of the power source unit and wherein the second sensor part, when maintained in the bearing cup part, is electrically connected to the bearing cup part.

7. The module according to claim 1, wherein the processor unit is disposed on said flexible printed circuit board sheet.

8. The module according to claim 1, further comprising a communication unit to wirelessly communicate dose size data to an external unit.

9. The module according to claim 1, wherein said first surface on which the plurality of individual electrical conductive sensor areas are arranged extend substantially perpendicular to or parallel with said axis of rotation (A).

10. The module according to claim 1 and in combination with a pen drug delivery device comprising a housing, a drug-filled non-interchangeable cartridge with a displaceable piston and an outlet and a piston rod to be advanced in a direction towards said piston to displace the piston and thereby expel a dosage of drug from the cartridge through the outlet, the piston rod rotating relative to the piston and housing during axial movement, and wherein the first sensor part of the module is directly or indirectly engaged with the housing such that no relative rotation between the housing and the first sensor part is possible, and the second sensor part of the module is directly or indirectly engaged with the piston rod such that no relative rotation between the piston rod and the second sensor part is possible.

11. A module in combination with a pen drug delivery device as in claim 10, wherein the piston rod during expelling of a dose exerts a distally directed force on the module, the force being transferred to the piston by the module, and wherein the power source unit constitutes the load bearing part transferring the force from the piston rod to the piston.

* * * * *